(12) United States Patent
Mutharasan et al.

(10) Patent No.: US 8,236,508 B2
(45) Date of Patent: Aug. 7, 2012

(54) DETECTING AND MEASURING LIVE PATHOGENS UTILIZING A MASS DETECTION DEVICE

(75) Inventors: Rajakkannu Mutharasan, West Chester, PA (US); Peter A. Nagy, Newtown Square, PA (US); Sen Xu, Philadelphia, PA (US)

(73) Assignees: Drexel University, Philadelphia, PA (US); Leversense, LLC, Newtown Square, PA (US)

( * ) Notice: Subject to any disclaimer, the term of this patent is extended or adjusted under 35 U.S.C. 154(b) by 290 days.

(21) Appl. No.: 12/361,922

(22) Filed: Jan. 29, 2009

(65) Prior Publication Data
US 2009/0235746 A1    Sep. 24, 2009

Related U.S. Application Data

(60) Provisional application No. 61/024,321, filed on Jan. 29, 2008.

(51) Int. Cl.
*C12Q 1/04* (2006.01)
*G01N 33/53* (2006.01)
(52) U.S. Cl. .............................. 435/7.1; 435/34; 435/38
(58) Field of Classification Search .................. None
See application file for complete search history.

(56) References Cited

U.S. PATENT DOCUMENTS

| | | | |
|---|---|---|---|
| 4,186,599 A | 2/1980 | Frick |
| 4,791,818 A | 12/1988 | Wilde et al. |
| 5,116,759 A | 5/1992 | Klainer et al. |
| 5,445,008 A | 8/1995 | Wachter et al. |
| 5,583,300 A | 12/1996 | Green et al. |
| 5,719,324 A | 2/1998 | Thundat et al. |
| 6,170,981 B1 | 1/2001 | Regnier et al. |
| 6,274,723 B1 | 8/2001 | Nilsen |
| 6,336,366 B1 | 1/2002 | Thundat et al. |
| 6,543,274 B1 | 4/2003 | Herrmann et al. |
| 6,589,727 B1 | 7/2003 | Kleneman et al. |
| 6,880,402 B1 | 4/2005 | Couet et al. |
| 7,195,909 B2 | 3/2007 | Kleneman et al. |
| 7,263,874 B2 | 9/2007 | Fitch et al. |
| 2003/0194697 A1 | 10/2003 | Kleneman et al. |
| 2003/0224551 A1 | 12/2003 | Kim et al. |
| 2005/0063882 A1 | 3/2005 | Centanni et al. |
| 2005/0112621 A1 | 5/2005 | Kim et al. |
| 2005/0164299 A1 | 7/2005 | Stewart |
| 2005/0229677 A1 | 10/2005 | Tuller et al. |
| 2005/0277852 A1 | 12/2005 | Shih et al. |
| 2006/0053870 A1 | 3/2006 | Berndt |
| 2006/0196253 A1 | 9/2006 | Crawley et al. |
| 2006/0223171 A1 | 10/2006 | Craighead et al. |
| 2006/0228657 A1 | 10/2006 | Masters et al. |
| 2007/0089515 A1 | 4/2007 | Shih et al. |
| 2007/0169553 A1 | 7/2007 | Mutharasan et al. |
| 2007/0218534 A1 | 9/2007 | Kleneman et al. |
| 2008/0034840 A1 | 2/2008 | Mutharasan et al. |
| 2008/0035180 A1 | 2/2008 | Mutharasan et al. |
| 2009/0078023 A1 | 3/2009 | Mutharasan et al. |

FOREIGN PATENT DOCUMENTS

| | | |
|---|---|---|
| EP | 0631319 A1 | 12/1994 |
| EP | 1536227 A2 | 6/2005 |
| WO | WO 98/50773 A2 | 11/1998 |
| WO | WO 2005/043126 A3 | 5/2005 |

OTHER PUBLICATIONS

Xu et al. Cell Viability Measurement Using 2',7'-Bis-(2-Carboxyethyl)-5-(-and-6)-Carboxyfluorescein Acetoxymethyl Ester and a Cantilever Sensor; Analytical Chemistry, vol. 83 (2011) pp. 1480-1483.*

Siber et al. Cross-Reactivity of Rabbit Antibodies to Lipopolysaccharides of *E. coli* J5 and Other Gram-Negative Bacteria; The Journal of Infectious Diseases, vol. 152, No. 5 (1985) pp. 954-964.*

Boulos et al. Live/Dead Baclight: Application of a New Rapid Staining Method for Direct Enumeration of Viable and Total Bacteria in Drinking Water; Journal of Microbiological Methods, vol. 37 (1999) pp. 77-86.*

Campbell et al., "Detection of pathogen *Escherichia coli* 0157:H7 using self-excited PZT-glass microcantilevers," Biosensors & Bioelectronics, Sep. 15, 2005, 21(3), 462-473.

Campbell, G.A., et al., "Use of Piezoelectric-Excited Millimeter-Sized Cantilever Sensors to Measure Albumin Interaction with Self-Assembled Monolayers of Alkanethiols Having Different Functional Headgroups," Anal. Chem., available online Feb. 28, 2006, 78(7), 2328-2334.

Campbell, G.A., et al., "Detection and quantification of proteins using self-excited PZT-glass millimeter-sized cantilever," Biosensors and Bioelectronics, 2005, 21, 597-607.

Campbell, G.A., et al., "Detection of airborne *Bacillus anthracis* spores by an integrated system of an air sampler and a cantilever immunosensor," Sensors and Actuators B Chemical, Nov. 15, 2007, available online May 1, 2007, 127(2), 376-382.

(Continued)

*Primary Examiner* — Rebecca Prouty
*Assistant Examiner* — Paul Martin
(74) *Attorney, Agent, or Firm* — Woodcock Washburn, LLP

(57) ABSTRACT

Extremely minute amounts of live pathogens are rapidly detected using a piezoelectric cantilever sensor. A single pathogen is detectable in about 30 minutes. Pathogen-specific antibodies are immobilized on the sensor surface. The sensor is exposed to a medium that potentially contains the target pathogen. When target pathogens are contained in the medium, both dead and live pathogen cells bind to the immobilized antibody on the sensor surface. The attached target pathogen cells are exposed to a pathogen discriminator capable of discriminating between live cells and dead cells by increasing the mass of live cells. Example pathogens include *Escherichia coli, Listeri monocytogene*, and *Salmonella enteritidis*. Example antibodies include those that bind to the pathogenic bacteria designated as ATCC 43251, ATCC 700375, and ATCC 31194. Example pathogen discriminators include intracellular pH indicating molecules.

16 Claims, 19 Drawing Sheets

OTHER PUBLICATIONS

Campbell, G.A., et al., "Detection of *Bacillus anthracts* spores and a model protein using PEMC sensors in a flow cell at 1 mL/MIN," Biosens Bioelectron, Jul. 15, 2006, Epub Jan. 19, 2006, 22(1), 78-85.

Campbell, G.A., et al., "PEMC sensor's mass change sensitivity in 20 PG/HZ under liquid immersion," Biosensors and Bioelectronics, Jul. 15, 2006, Epub Jan. 18, 2006, 22(1), 35-41.

Campbell, G.A., et al., "Piezoelectric-excited millimeter-sized cantilever (PEMC) sensors detect *Bacillus anthracis* at 300 spores/mL," Biosensors Bioelectronics, 2006, 21, 1684-1692.

Campbell, G.A., et al., "Detect of *Escherichia coli* O157:H7 in ground beef samples using piezoelectric excited millimeter-sized cantilever (PEMC) sensors," Biosens Bioelectron, Feb. 15, 2007, Epub Jul. 10, 2006, 22(7), 1296-1302.

Campbell, G.A., et al., "*Escherichia coli* O157:H7 detection limit of millimeter-sized PZT cantilever sensors in 700 cells/mL," Analytical Sci., Apr. 2005, 21, 11-13.

Campbell, G.A., et al., "Method of Measuring *Bacillus anthracis* spores in the presence of copious amounts of *Bacillus thuringiensis* and *Bacillus cereus*," Anal. Chem., published online Dec. 22, 2006, 79(3), 1145-1152.

Campbell, G.A., et al.,"A method of measuring *Escherichia coli* O157:H7 at 1 cell/mL in 1 liter sample using antibody functional piezoelectric-excited millimeter-sized cantilever sensor," Environ. Sci. Technol., published online Jan. 23, 2007, 41(5), 1668-1674.

Carr, D.W., et al., "Fabrication of nanoelectromechanical systems in single crystal silicon using silicon on insulator substrates and electron beam lithography," J. Vac. Sci. Technology, B, 15(6), 2760-2763, (1997).

Maraldo, D. et al., "Method for Label-Free Detection of Femtogram Quantities of Biologics in Flowing Liquid Samples," Anal. Chem., Apr. 1, 2007, 79(7), 2762-2770.

Maraldo, D., et al., "Method for Quantification of a Prostate Cancer Biomarker in Urine without Sample Preparation," Analytical Chem., Available online Sep. 15, 2007, 79(20), 7683-7690.

Maraldo, D., et al., "10-minute assay for detecting *Escherichia coli* O157:H7 in ground beef samples using piezoelectric-excited millimeter-sized cantilever (PEMC) sensors," J. of Food Protection, 2007, 70(7), 1670-1677.

Maraldo, D., et al., "Detection and confirmation of *Staphylococcal* enterotoxin B in apple juice and milk using Piezoelectric-excited Millimeter-sized cantilever (PEMC) sensors at 2.5 femtograms/mL," Analytical Chem., 2007, 79(20) 7636-7643.

Maraldo, D., et al., "Preparation-free method for detecting *Escherichia coli* O157:H7 in the presence of spinach, spring lettuce mix, and ground beef particulates," J. of Food protection, Nov. 2007, 70(11) 2651-2655.

Rijal, K., et al., "A method for measuring self-assembly of alkanethiols on gold at femtomolar concentrations," Langmuir, 2007, 23, 6856-6863.

Rijal, K., et al., "PEMC-based method of measuring DNA hybridization at femtomolar concentration directly in human serum and in the presence of copious non-complementary strands," Analytical Chem., 2007, 79, 7392-7400.

Seung S. Lee, et al., "Self-excited piezoelectric cantilever oscillators," Transducers '95-Eurosensors IX, The 8th Int. Conf. on Solid-State Sensors and Actuators, and Eurosensors IX, Stockholm, Sweden, Jun. 25-29, 1995, 417-420.

U.S. Appl. No. 11/747,183 by Mutharasan, et al., filed May 10, 2007.
U.S. Appl. No. 12/141,846 by Mutharasan, et al., filed Jun. 18, 2008.
U.S. Appl. No. 60/746,948 by Mutharasan, filed May 10, 2006.
U.S. Appl. No. 60/746,951 by Mutharasan, et al., filed May 10, 2006.
U.S. Appl. No. 60/807,020 by Mutharasan, et al., filed Jul. 11, 2006.
U.S. Appl. No. 60/944,592 by Mutharasan, filed Jun. 18, 2007.
U.S. Appl. No. 60/954,488 by Mutharasan, filed Aug. 7, 2007.

Wilson, L., et al., "Viscosity and density values from excitation level response of piezoelectric-excited cantilever sensors," Sensors and Actuators A, Jul. 20, 2007, 138, 44-51.

Yi Jeong W. et al., "In situ cell detection using piezoelectric lead zirconate titanate-stainless steel cantilevers," J Applied Physics, Jan. 1, 2003, 93(1), 619-625.

Zhou J. et al., "Zeolite-modified microcantilever gas sensor for indoor air quality control," Sensors and Actuators B, Oct. 1, 2003, 94(3), 337-342.

\* cited by examiner

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

Prior Art Structure

DETECTING AND MEASURING LIVE PATHOGENS UTILIZING A MASS DETECTION DEVICE

CROSS REFERENCE TO RELATED APPLICATIONS

The present application claims priority to U.S. Provisional Patent Application No. 61/024,321, entitled "METHOD FOR MEASURING LIVE PATHOGEN CONCENTRATION UTILIZING A PIEZOELECTRIC CANTILEVER SENSOR," filed Jan. 29, 2008, which is herein incorporated, in its entirety, by reference.

GOVERNMENT RIGHTS

This invention was made with government support under grant number NSF# CBET 0828987, Fund/Budget No. 235523, awarded by the National Science Foundation. The Government has certain rights in the invention.

TECHNICAL FIELD

The technical field generally relates to the detection and measurement of pathogens in a liquid or gas media. More particularly, the technical field relates to the use of a mass detection device, such as a piezoelectric cantilever sensor, to detect and measure live pathogen cells.

BACKGROUND

Pathogens can be dangerous to the public. A pathogen is an organism capable of producing an infectious disease in another organism. For example, *Escherichia coli* O157:H7 (*E. coli* O157:H7), a foodborne pathogen, is a facultative Gram-negative *bacillus*, and has been implicated in outbreaks of illness due to ingestion of meats, water, and uncooked fruits and vegetables. *E. coli* O157:H7 is capable of producing a variety of human illnesses which include hemolytic uremic syndrome and diarrhea. There have been several outbreaks of *E. coli* O157:H7 food poisoning in the US over the past few decades and the worldwide outbreaks caused by contaminated ground beef.

As another example, *Listeri monocytogenes*, a foodborne pathogen, is a Gram-positive bacterium known to cause meningitis in newborns. Pregnant mothers are often advised to not eat certain cheeses which may contain *Listeri monocytogenes*.

Another example pathogen is *Salmonella enteritidis*. *Salmonella enteritidis* is a Gram-negative bacterium known to cause salmonellosis and typhoid fever. *Salmonella enteritidis* can be foodborne (e.g., raw chicken, undercooked eggs, etc.), or can be transmitted via a fecal-oral route (e.g., via contaminated water and person-person contact). In fact, vacuum cleaner bags have be known to be contaminated with *Salmonella enteritidis*.

Current methods for detecting pathogens are time consuming and not very sensitive. Traditionally, detection of pathogens has involved sample collection and enrichment, followed by isolation and identification of the targeted pathogen. Many current detection approaches lack sensitivity and specificity, and often takes 24-96 hours to identify the target pathogen. Current detection devices, such as fiber optic biosensors for example, due to a lack of detection sensitivity, require pre-enrichment of a sample because the target pathogen is present in concentrations below the device's limit of detection. Additional problems associated with current detection methods and devices include high cost and the need for specifically-trained personnel.

SUMMARY

A mass detection device, such as a piezoelectric cantilever sensor, is configured as a metabolic activity measurement device capable of quickly (e.g., 30 minutes) measuring extremely small changes in mass (e.g., one femtogram, $10^{-15}$ g) of a pathogen without requiring enrichment. Amounts of live cells and dead cells can be determined. In an example embodiment, to achieve selectivity, antibodies that are specific to a respective target pathogen are immobilized on the sensor surface. The sensor is exposed to a medium that potentially contains the target pathogen. The medium can contain the target pathogen, can contain no target pathogen, or can contain a combination of target pathogen and non-target pathogen (pathogens other than the target pathogen). Non-specific adsorption, that is adsorption of non-target pathogens, is reduced (and in some cases minimized or prevented entirely) due to flow and active sensor surface vibration. When target pathogens are contained in the medium, both dead and live target pathogen cells bind to the immobilized antibody on the sensor surface. In an example embodiment, the sensor is rinsed. After rinsing, the attached target pathogen cells are exposed to a pathogen discriminator. In an example embodiment, the pathogen discriminator discriminates between live cells and dead cells by increasing the mass of live cells. In an example embodiment, the pathogen discriminator comprises a pH indicating molecule, BCECF-AM, (e.g., 2',7'-bis-(2-carboxyethyl)-5-(and -6)-carboxy-fluorescein, acetoxymethyl ester), that partitions and accumulates in live cells, and not in dead cells. Accumulation of BCECF-AM in the live target pathogen cells results in an increase of mass accumulated on the sensor surface. The change in mass is detected by the sensor, and utilized to determine the amount of live target pathogen cells accumulated on the sensor. This provides an indication of the presence of live target pathogen in the medium. This also provides a measure of the amount of live target pathogen in the medium.

BRIEF DESCRIPTION OF THE DRAWINGS

The foregoing summary, as well as the following detailed description, is better understood when read in conjunction with the appended drawings.

DETAILED DESCRIPTION OF ILLUSTRATIVE EMBODIMENTS

Figure 1:
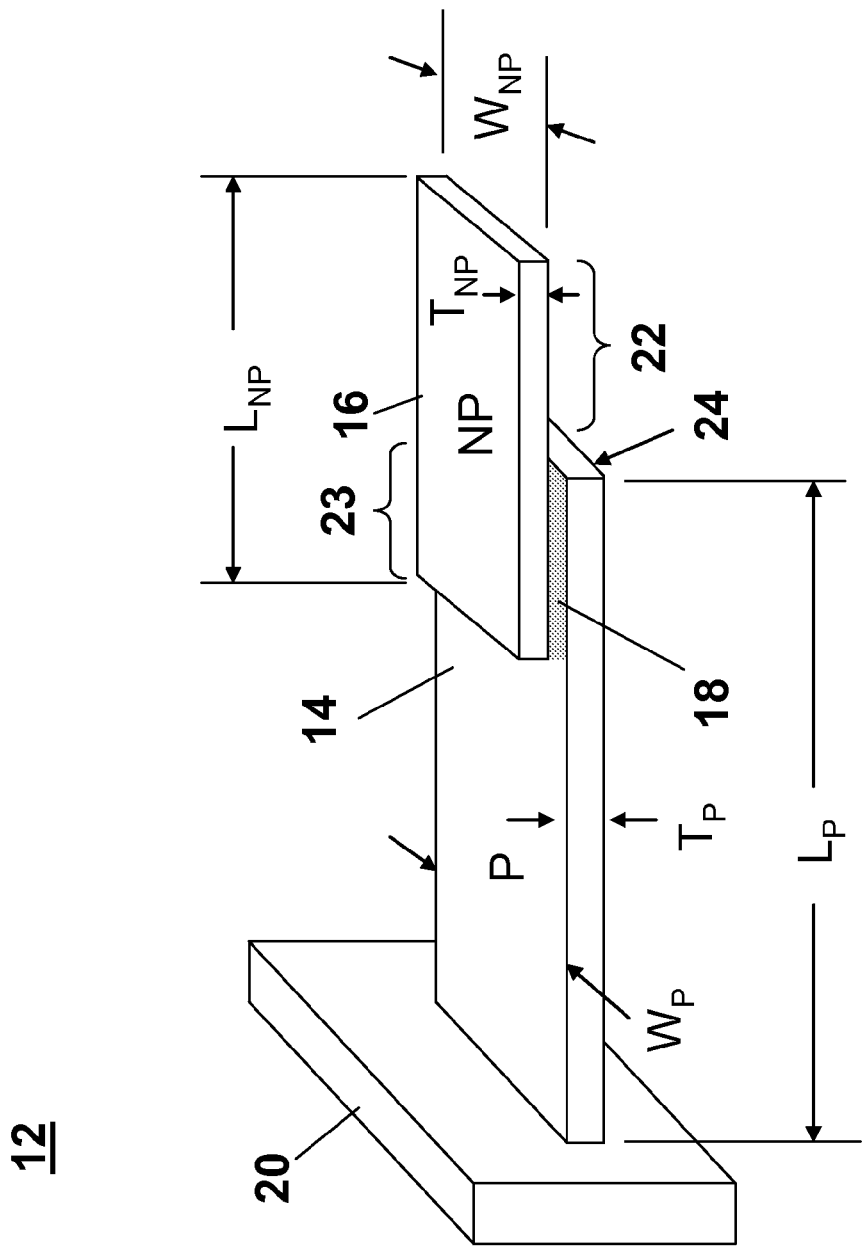
FIG. 1 is an illustration of an example configuration of a self-exciting, self-sensing piezoelectric cantilever sensor.

A rapid method for detecting and measuring live pathogens utilizes a mass detection device. Results are obtainable in approximately 30 minutes. Quantities as small as one femtogram ($10^{-15}$ g) of a pathogen (e.g., one cell) are detectable. The detection and measurement process utilizes label-free reagents and a simple measurement format. The ability to rapidly obtain an indication of the presence of live pathogens, in food samples for example, allows a food product handling facility to make suitable corrections to operations on the factory floor. This can prevent the distribution of contaminated food. This rapid and sensitive measurement can be used in a multitude of practical situations thereby reducing the incidences of exposure of the public to contaminated food.

In an example configuration, the mass detection device is a piezoelectric cantilever sensor. In another example configuration, the mass detection device is a piezoelectric-excited millimeter-sized cantilever sensor (PEMC). In this example configuration, the piezoelectric cantilever sensors is a millimeter-sized resonant mode cantilever that exhibits a high-order mode that is more sensitive than any reported biosensors under liquid immersion and flow conditions. Measurements of mass changes of a femtogram are obtainable. Operation of the cantilever sensor incorporates flow and vibration of the sensor surface that tends to reduce or minimize non-specific adsorption (adsorption of non-target pathogens).

Utilizing the piezoelectric cantilever sensor as a metabolic activity measurement device, in an example process, specific antibodies, known to bind to specific pathogens, are immobilized on the surface of the sensor. The antibodies are immobilized on the sensor surface to achieve selectivity and recognition of the target pathogen (or target pathogens). The attached cells are then exposed to a pathogen discriminator. The pathogen discriminator is used to discriminate between live cells and dead cells. The pathogen discriminator possesses the ability to increase the mass of live cells. In an example embodiment, the pathogen discrimination comprises a non-fluorescent molecule (2',7'-bis-(2-carboxyethyl)-5-(and -6)-carboxyfluorescein, acetoxymethyl ester (BCECF-AM) that partitions and accumulates as a result of the action of intracellular esterases in live cells, and not in dead cells. The resulting change in mass due to BCECF-AM accumulation (due to its high charge per molecule upon hydrolysis due to esterase action) is detected via the piezoelectric cantilever sensor and provides a measure for the presence of live pathogens. Although BCECF-AM will diffuse into dead cells, it does not accumulate because esterase activity and metabolic energy are required to hydrolyze uncharged BCECF-AM to charged and fluorescent BCECF. It is estimated that 1 pg ($10^{-12}$ g) of live pathogen will accumulate as much as 10 femtogram of BCECF. In accordance with this estimation, a single live cell is detectable. The high sensitivity of the piezoelectric sensor implies that a single pathogen is measurable in a sample as small as a few milliliters (mL).

In another example embodiment, as described in more detail below, the presence of live pathogens is ascertained by growing attached pathogen cells on the sensor surface. This, too causes a change in mass, which is detectable and measurable via a change in resonance frequency. As described in more detail below, the piezoelectric cantilever sensor is utilized as a metabolic activity measurement device to detect and measure live pathogens.

The piezoelectric cantilever utilized to detect and measure live pathogens, in an example configuration, is a piezoelectric cantilever sensing device that includes a piezoelectric layer and a non-piezoelectric layer attached to the piezoelectric layer such that a distal end of the non-piezoelectric layer extends beyond a distal end of the piezoelectric layer or a distal end of the piezoelectric layer extends beyond a distal end of the non-piezoelectric layer. The piezoelectric cantilever provides the ability to detect and measure extremely small amounts of an analyte (e.g., pathogen). The piezoelectric cantilever sensor can be utilized to detect and measure an analyte immersed in a liquid and an analyte contained in a gas or vacuum. In various configurations, the piezoelectric layer, the non-piezoelectric layer, or both are anchored to at least one base. The piezoelectric layer and the non-piezoelectric layer can be of varying widths, lengths, and thicknesses. Electrodes are operatively associated with the piezoelectric layer. The piezoelectric cantilever sensor is utilized to sense mass change. To determine the mass of an analyte (e.g., pathogen) on the sensing apparatus, the resonance frequency of the mechanical member of the cantilever sensor is measured. The measured resonance frequency is compared with a baseline resonance frequency to determine a difference in frequency. The difference in the measured resonance frequency and the baseline resonance frequency is indicative of an amount of mass of analyte accumulated (e.g., bound, adsorbed, absorbed) on the piezoelectric cantilever sensor.

Pathogens can be directly or indirectly bound to the surface of the non-piezoelectric portion of the piezoelectric cantilever sensor. Binding of an pathogen to the non-piezoelectric portion of the piezoelectric cantilever sensor results in a change in mass of the piezoelectric cantilever sensor, a change in stiffness of the piezoelectric cantilever sensor, or a combination thereof. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the piezoelectric cantilever sensor is immersed in a liquid, are detectable and measurable. Resonance frequency changes, wherein at least a portion of the piezoelectric cantilever sensor is immersed in a gas or a vacuum, also are detectable and measurable.

The piezoelectric cantilever sensor is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The piezoelectric cantilever sensor is operateable at relative high frequencies in liquid media, gas media, and a vacuum. The piezoelectric cantilever sensor thus provides extreme sensitivity to mass changes. The piezoelectric cantilever sensor is especially suitable for analytes that are present at very low concentrations in media such as pathogens in body fluids, water, and food materials, for example.

The piezoelectric cantilever sensor described herein provides the ability to detect changes in mass accumulated thereon as small as 100 attogram/Hz ($100 \times 10^{-18}$ grams/Hertz) or less when immersed in a liquid media. Thus, with respect to detecting changes in mass, the piezoelectric cantilever sensor is approximately 1 million times more sensitive than a quartz crystal micro-cantilever sensor, approximate 100,000 times more sensitive than standard analytical instruments.

The piezoelectric cantilever sensor is operable in media having relatively high flow rates. The piezoelectric cantilevers sensors is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of certain cell types in body fluids (e.g., circulating tumor cells), the detection of biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), the detection of markers of explosives such as trinitrotoluene, the presence of dinitrotoluene, and the detection of airborne and waterborne toxins. The piezoelectric cantilever sensor also can be used for the detection of biological entities at picogram levels, and for the detection of protein-protein interactions, both steady state and kinetic.

Pathogens, such as *E-coli* for example, are detectable utilizing the piezoelectric cantilever sensor. Detection of a model protein, lipoprotein, DNA, and/or RNA at a concentration 1.0 femtogram per mL ($10^{-15}$ grams) and pathogens at 1 pathogen/mL, respectively is achievable by measuring directly in liquid using the piezoelectric cantilever sensor immobilized with antibodies specific to the target analyte at a frequency of about 1 to 2 MHz. The piezoelectric cantilever sensor is capable of detecting a target analyte without false positives or negatives even when contaminating entities are present. The piezoelectric cantilever sensor described herein is particularly advantageous when utilized with a raw sample, and no preparation, concentrating step, and/or enrichment of any type. Detection of an analyte utilizing the piezoelectric cantilever sensor can be conducted directly in raw samples under flow conditions, such as 0.5 to 10.0 mL/minute for example. If clean samples are available, such as in a laboratory environment, detection at 1 femtogram/mL is achievable. This sensitivity is approximately 100 times more sensitive than the sensitivity associated with known optical techniques.

As described below, the sensitivity of the piezoelectric cantilever sensor is due in part to the geometric design thereof. The relative lengths and widths of the piezoelectric and non-piezoelectric layers of the piezoelectric cantilever sensor determine the sensitivity, and also the shape of the peak of the frequency spectrum provided by the piezoelectric cantilever sensor. As described in more detail below, the piezoelectric cantilever sensor comprises a piezoelectric layer and a non-piezoelectric layer coupled together such that a portion of the piezoelectric layer extends beyond the non-piezoelectric layer, or a portion of the non-piezoelectric layer extends beyond the piezoelectric layer, or a combination thereof. Thus, the piezoelectric layer and the non-piezoelectric layer are not coextensive. That is, the piezoelectric cantilever sensor is configured such that an entire surface of the non-piezoelectric layer is not coupled to an entire surface of the piezoelectric layer.

The sensitivity of the piezoelectric cantilever sensor is due in part to utilizing the piezoelectric layer of the cantilever sensor for both actuation and sensing electromechanical properties of the piezoelectric layer of the piezoelectric cantilever sensor. At resonance, the oscillating cantilever concentrates stress in the piezoelectric layer toward a base portion of the piezoelectric cantilever. This results in an amplified change in the resistive component of the piezoelectric layer, and a large shift in resonance frequency. Directing this stress to a portion of the piezoelectric layer having a low bending modulus (e.g., more flexible) allows for exploitation of the associated shift in resonance frequency to detect extremely small changes in mass of the piezoelectric cantilever sensor. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cubed power of thickness.

The piezoelectric cantilever sensor described herein utilizes a cantilever-structure. The piezoelectric cantilever sensor described herein is not a resonating or bending mode microcantilever. It is not a microcantilever and it is not an atomic force microscopy (AFM)-like device. It does not operate in the bending mode. The piezoelectric cantilever sensor exhibits femtogram ($10^{-15}$ g) sensitivity. It is electrically actuated and electrically sensed. Since it does not require sophisticated methods to fabricate, it is inexpensive. In an example configuration, the piezoelectric cantilever is a macro-cantilever that comprises a piezoelectric ceramic lead zirconate and titanate (PZT) layer bonded to a non-piezoelectric layer of a few millimeters in length and 1 mm width forming a composite cantilever. The direct piezoelectric effect is used to excite the cantilever and to sense the resulting resonance response via the same PZT film. When an electric field is applied across the thickness of the PZT film, it extends along its length causing the underlying glass to bend. If the applied field is alternated periodically, the composite cantilever vibrates. The natural frequency of the cantilever depends on the flexural modulus and mass density of the composite cantilever. At resonance, the cantilever undergoes significantly higher stresses when the exciting electric field is at the sensor's natural mechanical resonance frequency. The PZT layer exhibits a sharp change in electrical impedance and can be measured by the phase angle measurement. Sensitivity on the order of 1 to 138 ag (attogram, $10^{-18}$)/Hz are obtainable.

FIG. 1 is an illustration of a piezoelectric cantilever sensor 12 comprising a piezoelectric portion 14 and a non-piezoelectric portion 16. Piezoelectric portions are labeled with an uppercase letter p ("P"), and non-piezoelectric portions are labeled with the uppercase letters np ("NP"). The piezoelectric cantilever sensor 12 depicts an embodiment of an unanchored, overhang, piezoelectric cantilever sensor. The piezoelectric cantilever sensor 12 is termed "unanchored" because the non-piezoelectric layer 16 is not attached to the base portion 20. The piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 0.1 mm to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
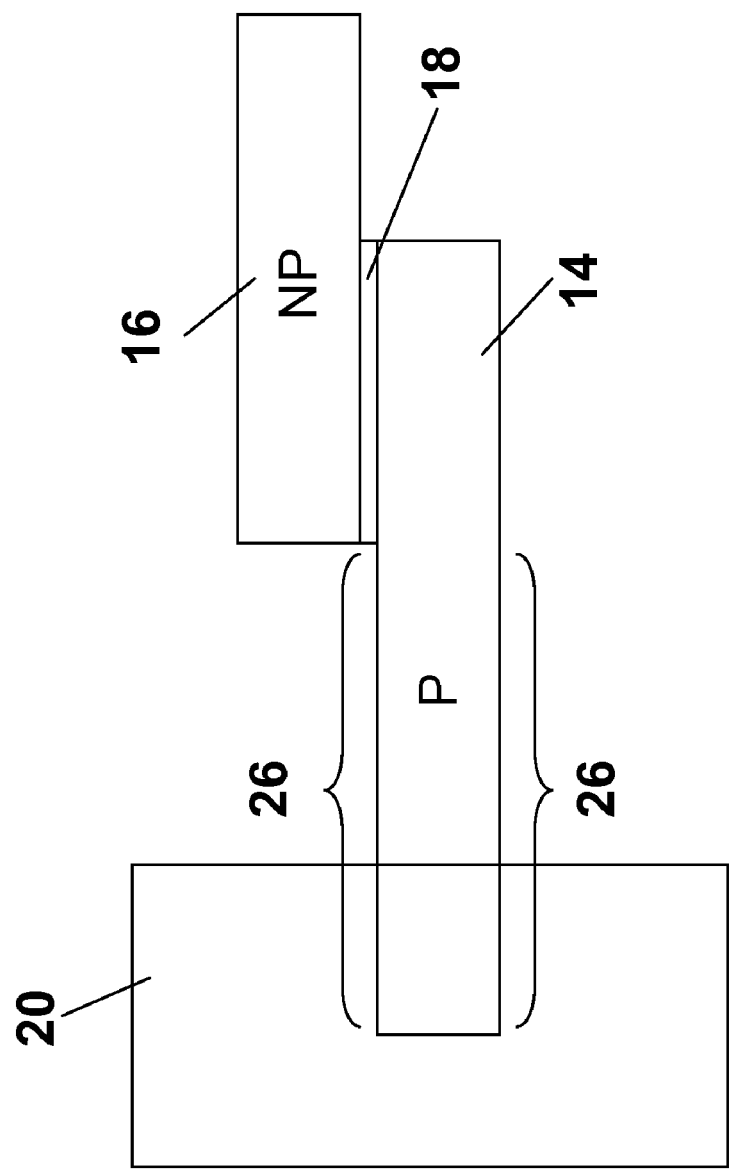
FIG. 2 is a cross-sectional view of an example self-exciting, self-sensing piezoelectric cantilever sensor depicting electrode placement regions for electrodes operationally associated with the piezoelectric layer.
Figure 3:
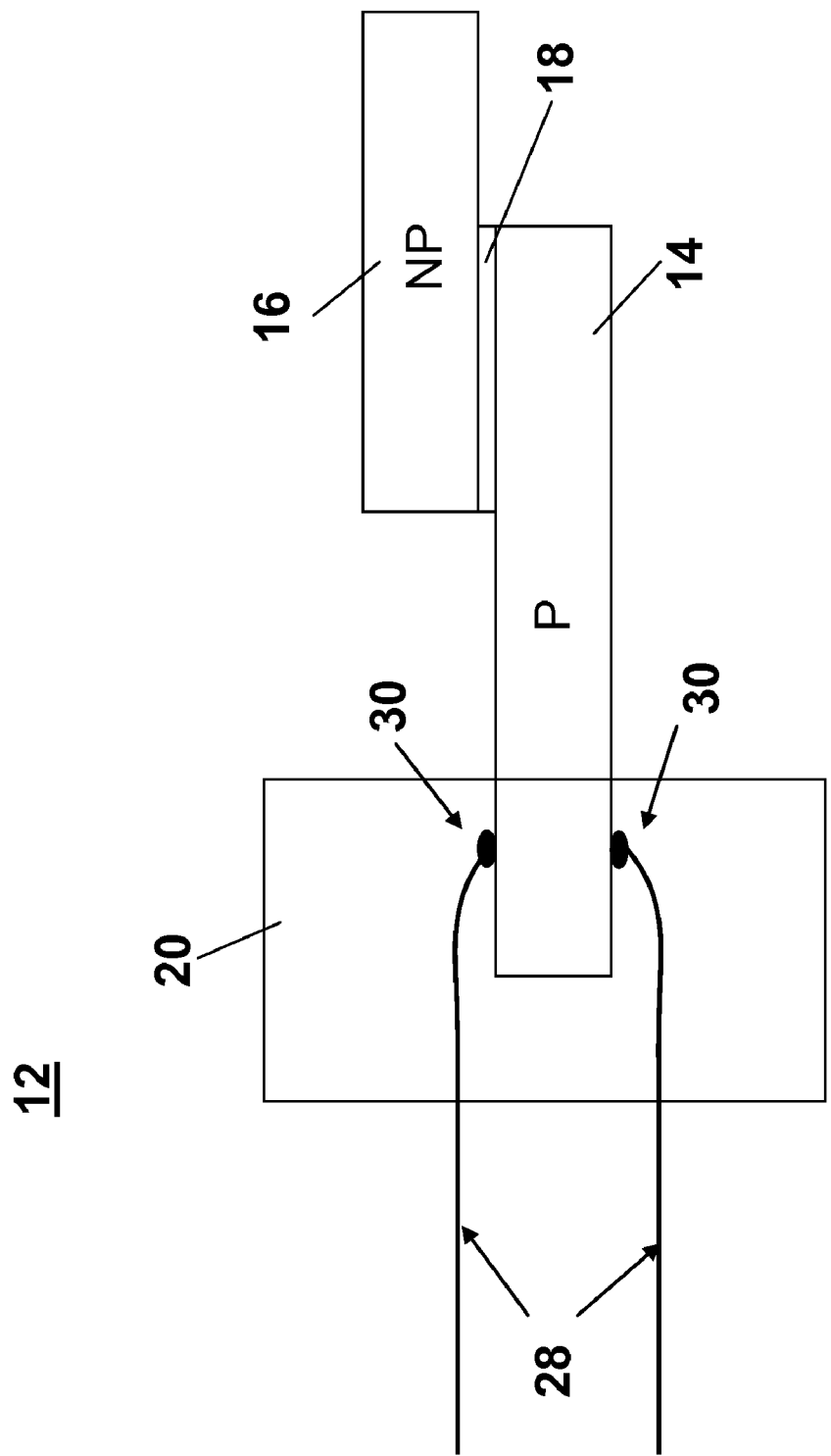
FIG. 3 is a cross-sectional view of an example self-exciting, self-sensing piezoelectric cantilever sensor showing depicting example electrode placement within a base portion of the self-exciting, self-sensing piezoelectric cantilever sensor.
Figure 4:
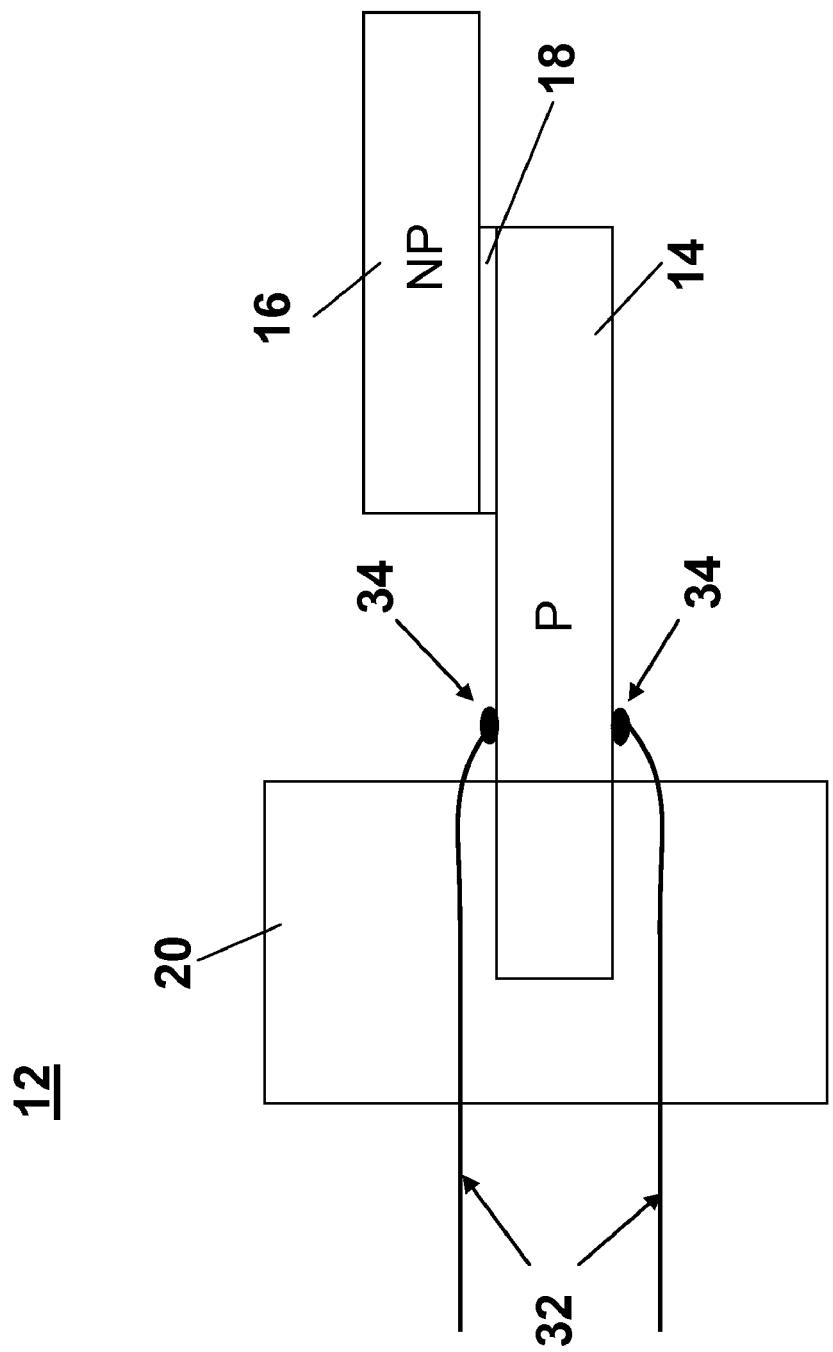
FIG. 4 is a cross-sectional view of an example self-exciting, self-sensing piezoelectric cantilever sensor showing depicting example electrode placement not within a base portion of the self-exciting, self-sensing piezoelectric cantilever sensor.

FIG. 2 is a cross-sectional view of the piezoelectric cantilever sensor 12 depicting electrode placement regions 26 for electrodes operationally associated with the piezoelectric portion 14. Electrodes can be placed at any appropriate location on the piezoelectric portion of the piezoelectric cantilever sensor as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20 and not overlapped by the non-piezoelectric portion 16. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location. In an example embodiment, electrodes are operatively located near a location of concentrated stress in the piezoelectric layer 14. As described above, the sensitivity of the piezoelectric cantilever sensor is due in part to advantageously directing (concentrating) the stress in the piezoelectric layer 14 and placing electrodes proximate thereto. The configurations of the piezoelectric cantilever sensor described herein (and variants thereof) tend to concentrate oscillation associated stress in the piezoelectric layer 14. At resonance, in some of the configurations of the piezoelectric cantilever sensor, the oscillating cantilever concentrates stress in the piezoelectric layer 14 toward the base portion 20. This results in an amplified change in the resistive component of the piezoelectric layer 14, and a large shift in resonance frequency at the locations of high stress. Directing this stress to a portion of the piezoelectric layer 14 having a low bending modulus (e.g., more flexible) allows for exploitation of the associated shift in resonance frequency to detect extremely small changes in mass of the piezoelectric cantilever sensor. Thus, in example configurations of the piezoelectric cantilever sensor, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the piezoelectric cantilever sensor. In other example configurations of the piezoelectric cantilever sensor electrodes are positioned proximate the location of concentrated stress in the piezoelectric layer regardless of the proximity of the concentrated stress to a base portion of the piezoelectric cantilever sensor.

Figure 5:
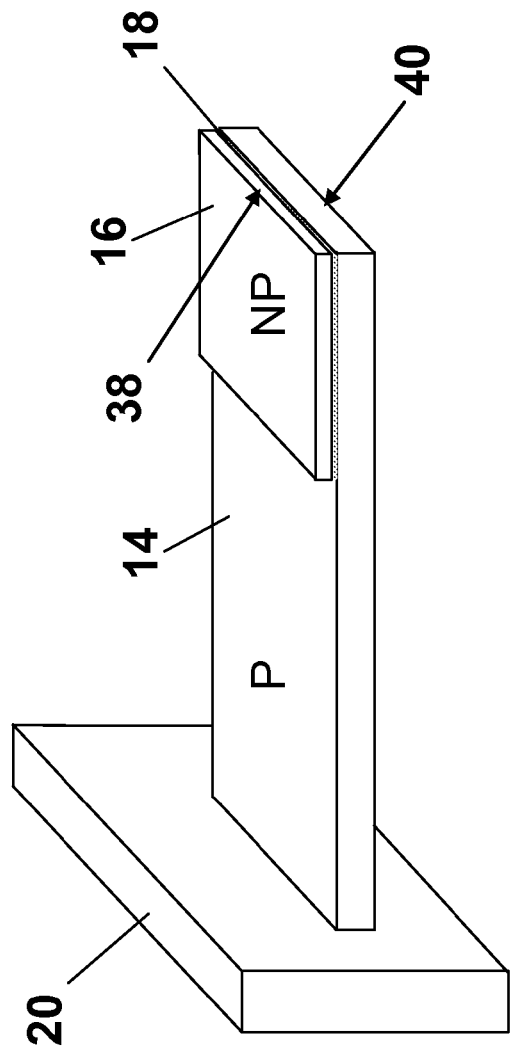
FIG. 5 is an illustration of an example configuration of a self-exciting, self-sensing piezoelectric cantilever sensor wherein the distal end of the piezoelectric layer is flush with the distal end of the non-piezoelectric layer.

The piezoelectric cantilever sensor can be configured in accordance with a plurality of configurations, some of which are depicted in FIG. 5 through FIG. 16. It is to be understood however, that the configurations depicted herein do not represent all possible configurations, but rather a representative sample of configurations of the piezoelectric cantilever sensor. FIG. 5 is an illustration of an example configuration 36 of an unanchored piezoelectric cantilever sensor wherein the distal end 40 of the piezoelectric portion 14 is flush with the distal end 38 of the non-piezoelectric portion 16. The piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

Figure 6:
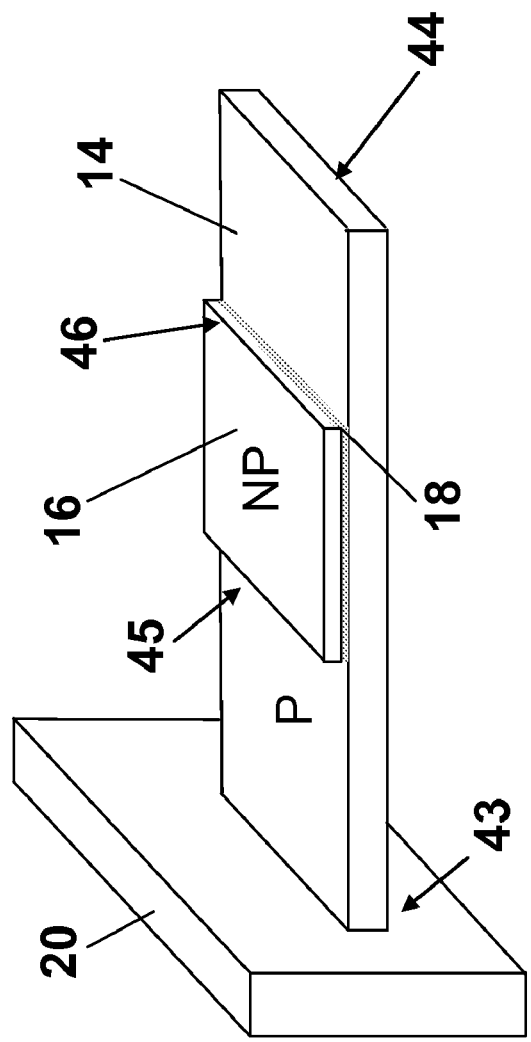
FIG. 6 is an illustration of an example configuration of a self-exciting, self-sensing piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

FIG. 6 is an illustration of an example configuration 42 of an unanchored piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

The piezoelectric cantilever sensor also can be configured to comprise multiple base portions. Example configurations of the piezoelectric cantilever sensor comprising multiple base portions are depicted in FIG. 7 through FIG. 14. Configuring the piezoelectric cantilever sensor to comprise multiple base portions is not intuitive because the expectation of one skilled in the art would be that affixation of both ends of the piezoelectric cantilever sensor would provide a poor response as a result of the restrictions of the displacement of the piezoelectric cantilever sensor as a result of its affixation to the multiple base portions. For configurations of the piezoelectric cantilever sensor comprising two base portions, in an example embodiment, the stress of in the piezoelectric portion is measured, rather than the displacement of the piezoelectric portion. Configuring the piezoelectric cantilever sensor to comprise two base portions provides a stable and robust sensor that can perform under relatively high media flow conditions and provide excellent mass change sensitivity. Along with providing a mechanically robust piezoelectric cantilever sensor that can withstand a relatively wide range of media flow conditions with minimal determination in performance, configuring the piezoelectric cantilever sensor to comprise two base portions provides a fundamental frequency (e.g., greater than 100 kHz) that is three to four times higher than a cantilever sensor having a single base portion and of similar dimensions.

Figure 7:
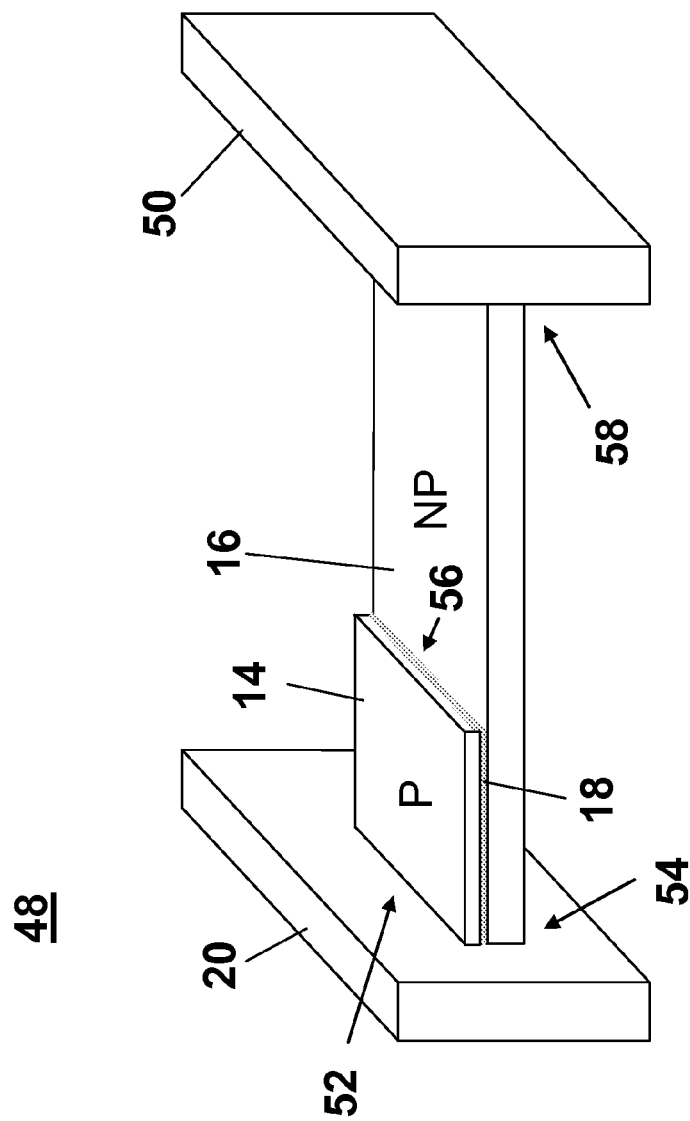
FIG. 7 is an illustration of an example configuration of a self-exciting, self-sensing piezoelectric cantilever sensor having two base portions.

FIG. 7 is an illustration of an example configuration 48 of an anchored piezoelectric cantilever sensor comprising two base portions 20, 50. The piezoelectric cantilever sensor 48 is termed "anchored" because the non-piezoelectric portion 16 is attached to the base portion 20. In the configuration depicted in the piezoelectric cantilever sensor 48, both the proximate end 52 of the piezoelectric portion 14 and the proximate end 54 of the non-piezoelectric portion 16 are attached to the base portion 20. The piezoelectric portion and the non-piezoelectric portion can be attached to the base portion via any appropriate means. The distal end 58 of the non-piezoelectric portion 16 also is attached to the base portion 50. The distal end 58 of the non-piezoelectric portion 16 extends beyond the distal portion 56 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 8:
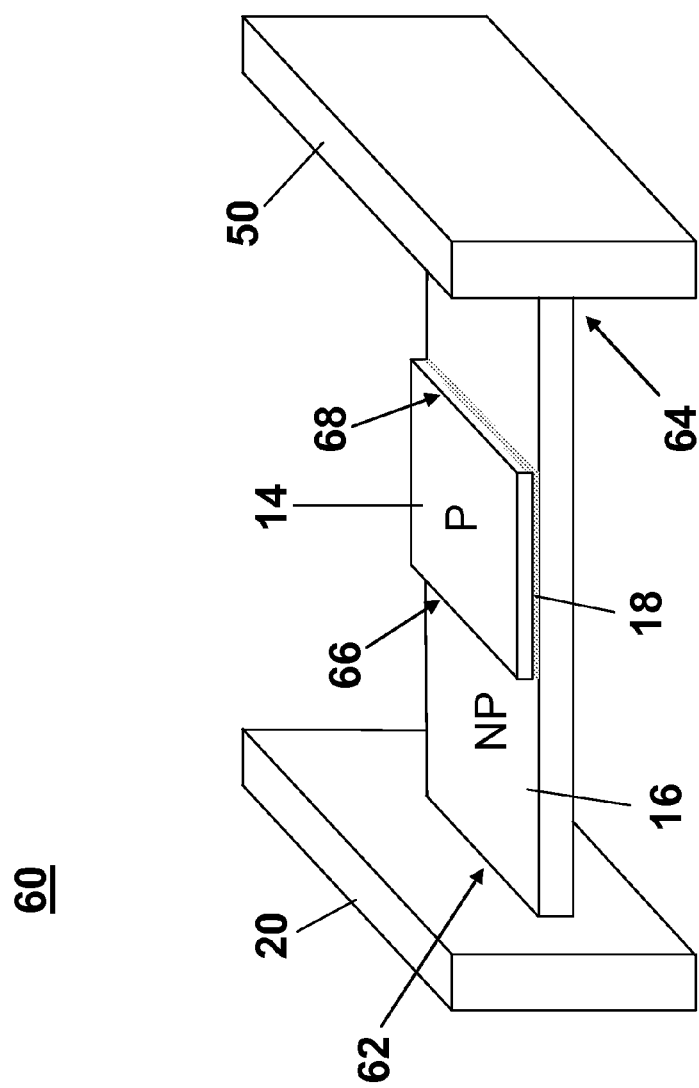
FIG. 8 is an illustration of another example configuration of a self-exciting, self-sensing piezoelectric cantilever sensor, wherein the piezoelectric layer is not attached to either base portion.

FIG. 8 is an illustration of an example configuration 60 of an anchored piezoelectric cantilever sensor comprising two base portions 20, 50, wherein the piezoelectric portion 14 is not attached to either base portion 20 or base portion 50. In the configuration depicted in the piezoelectric cantilever sensor 60, the proximate end 62 of the non-piezoelectric portion 16 is attached to the base portion 20 and the distal end 64 of the non-piezoelectric portion 16 is attached to the base portion 50. The proximate end 62 of the non-piezoelectric portion 16 extends beyond the proximate end 66 of the piezoelectric portion 14 and the distal end 64 of the non-piezoelectric portion 16 extends beyond the distal end 68 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 9:
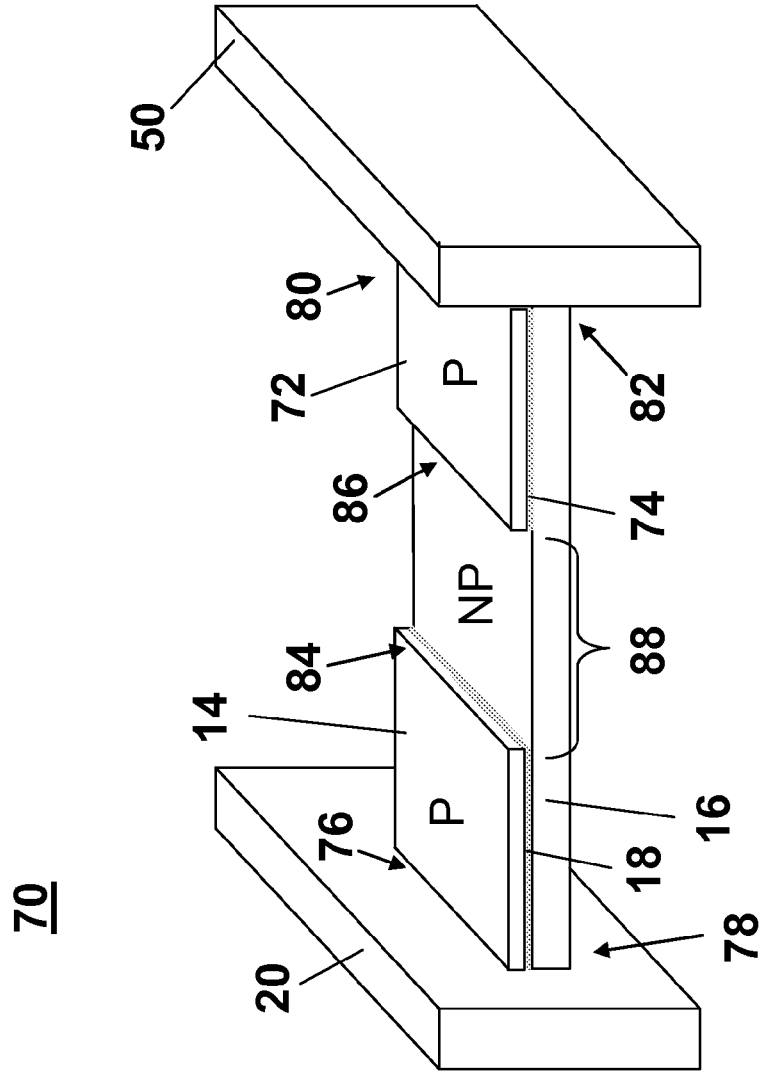
FIG. 9 is an illustration of an example configuration of a self-exciting, self-sensing piezoelectric cantilever sensor having the piezoelectric layer anchored at two ends.

FIG. 9 is an illustration of an example configuration 70 of an anchored piezoelectric cantilever sensor comprising two base portions 20, 50, comprising two piezoelectric portions 14, 72, and comprising two adhesive portions 18, 74. In the configuration depicted in the piezoelectric cantilever sensor 70, the proximate end 76 of the piezoelectric portion 14 and the proximate end 78 of the non-piezoelectric portion 16 are attached to the base portion 20. The distal end 80 of the piezoelectric portion 72 and the distal end 82 of the non-piezoelectric portion 16 are attached to the base portion 50. The proximate end 78 of the non-piezoelectric portion 16 extends beyond the proximate end 86 of the piezoelectric portion 72. The distal end 82 of the non-piezoelectric portion 16 extends beyond the distal end 84 of the piezoelectric portion 14. The distal end 84 of the piezoelectric portion 14 and the proximate end 86 of the piezoelectric portion 72 form a space 88 therebetween. The piezoelectric portion 14 is coupled to the non-piezoelectric portion 16 via adhesive portion 18. The piezoelectric portion 72 is coupled to the non-piezoelectric portion 16 via adhesive portion 74. The adhesive portions 18 and 74 are positioned, respectively, between the overlapping portions of the piezoelectric portion 14 and the non-piezoelectric portion 16, and the piezoelectric portion 72 and the non-piezoelectric portion 16.

Figure 10:
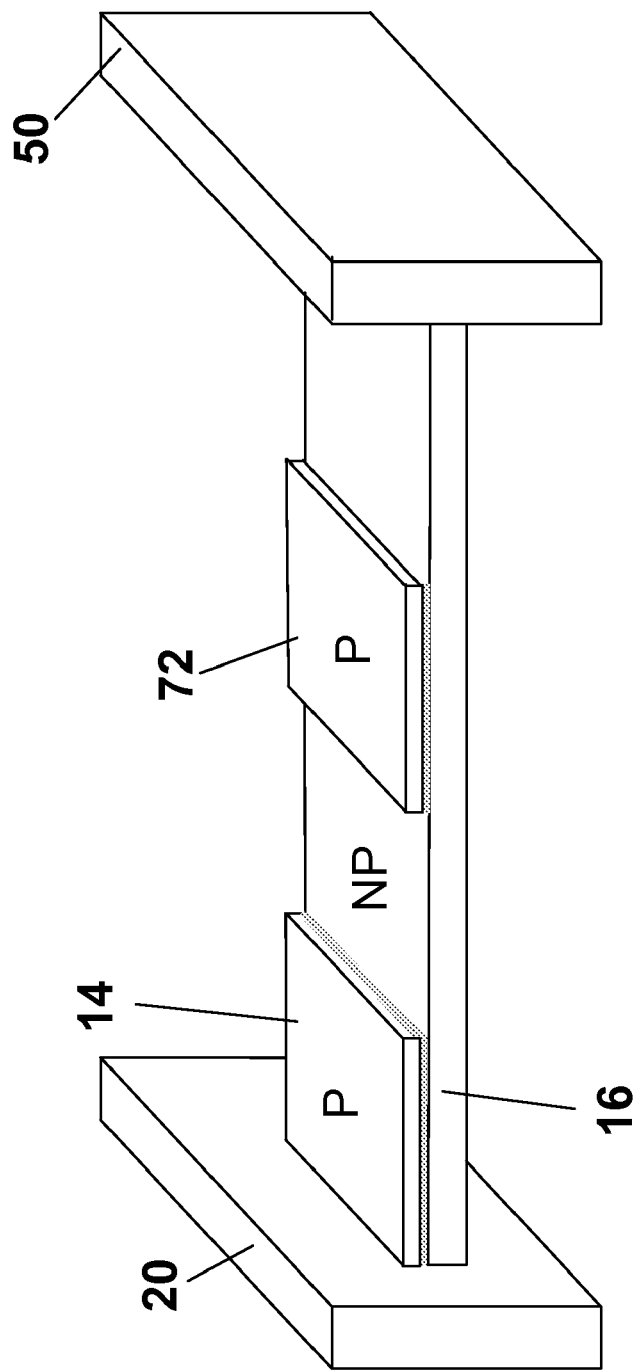
FIG. 10 is an illustration of an example configuration of a self-exciting, self-sensing piezoelectric cantilever sensor wherein the piezoelectric layer comprises two portions, one of which is anchored.
Figure 11:
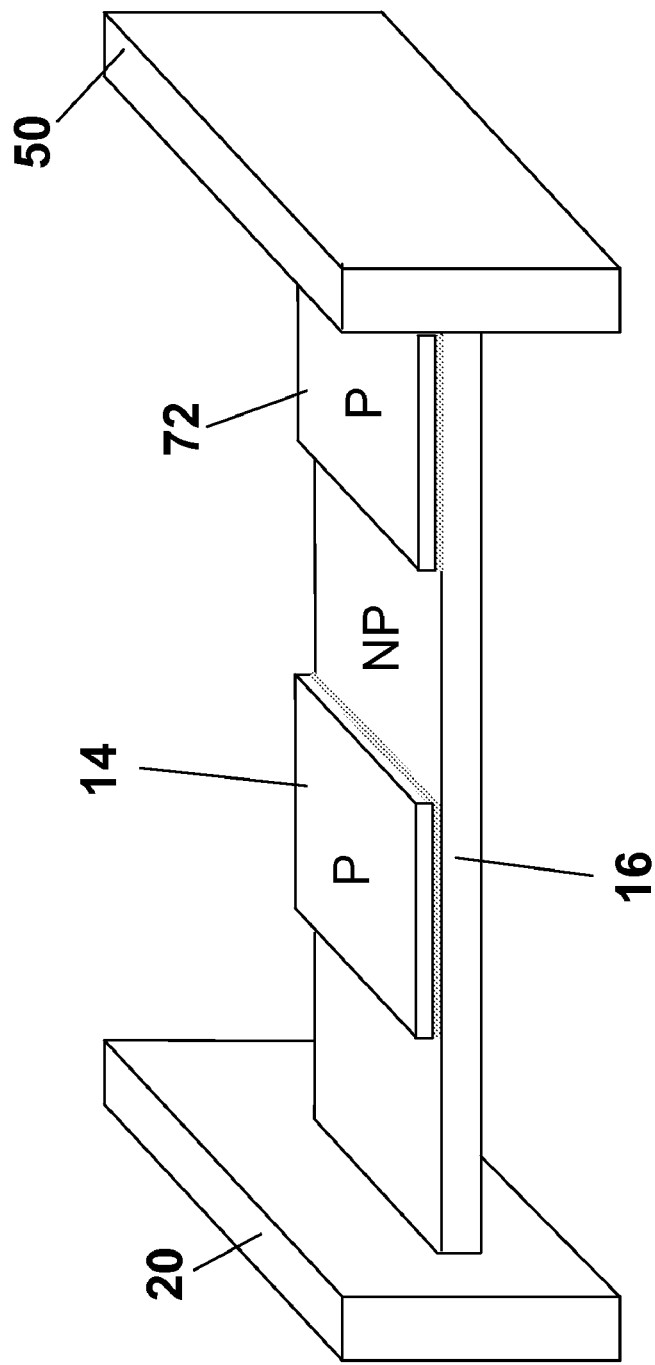
FIG. 11 is another illustration of an example configuration of a self-exciting, self-sensing piezoelectric cantilever sensor wherein the piezoelectric layer comprises two portions, one of which is anchored.
Figure 12:
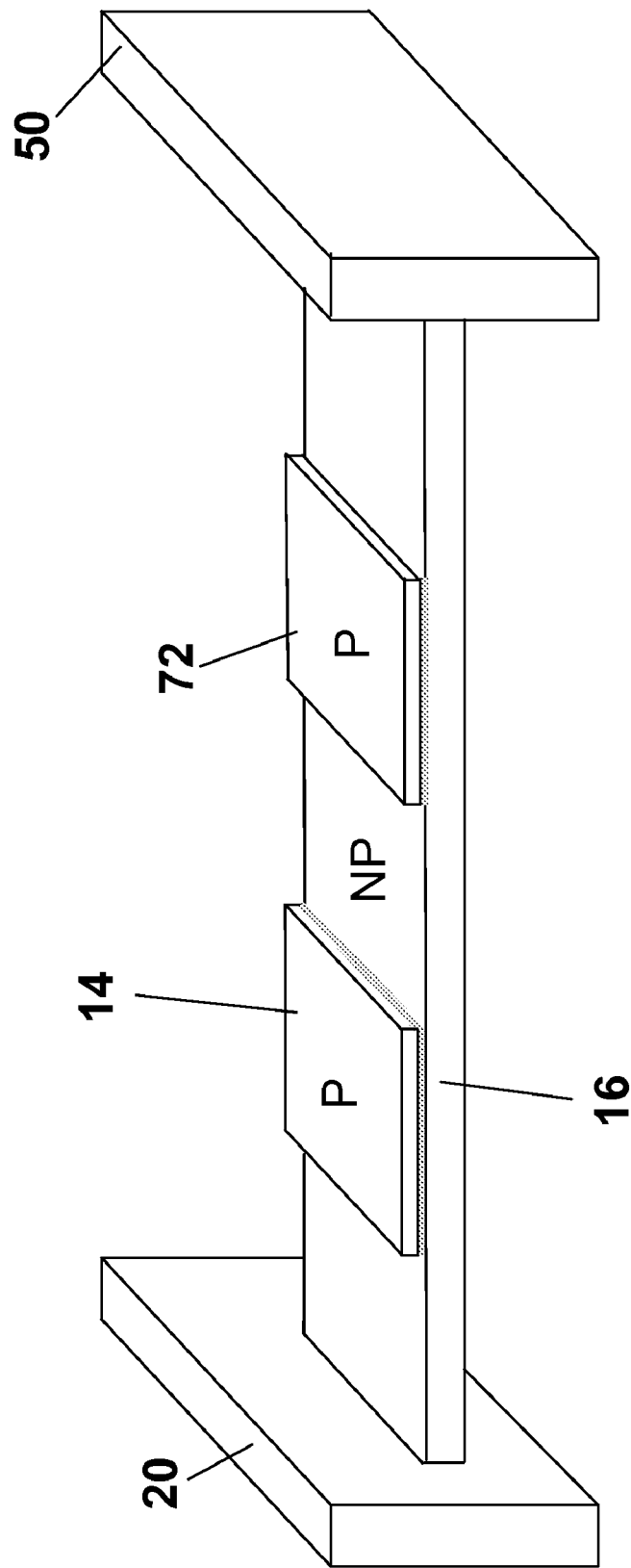
FIG. 12 is an illustration of an example configuration of a self-exciting, self-sensing piezoelectric cantilever sensor wherein the piezoelectric layer comprises two portions, neither which is anchored.

In various alternate example configurations of the configuration 70 depicted in FIG. 9, only one of the piezoelectric portions 14, 72 is attached to a respective base portion 20, 50. For example, in one example configuration as depicted in FIG. 10, the piezoelectric portion 14 is attached to the base portion 20 and the piezoelectric portion 72 is not attached to the base portion 50. In another example configuration, as depicted in FIG. 11, the piezoelectric portion 72 is attached to the base portion 50 and the piezoelectric portion 14 is not attached to the base portion 20. In yet another example configuration, as depicted in FIG. 12, neither the piezoelectric portion 14 nor the piezoelectric portion 72 is attached to a respective base portion 20, 50. In the various example configurations in which a piezoelectric layer comprises multiple portions, electrodes can be attached to any appropriate piezoelectric portion or portions. For example, in the example configuration depicted in FIG. 9, FIG. 10, FIG. 11, and FIG. 12, electrodes can be attached to piezoelectric portion 14, piezoelectric portion 72, or a combination thereof.

Figure 13:
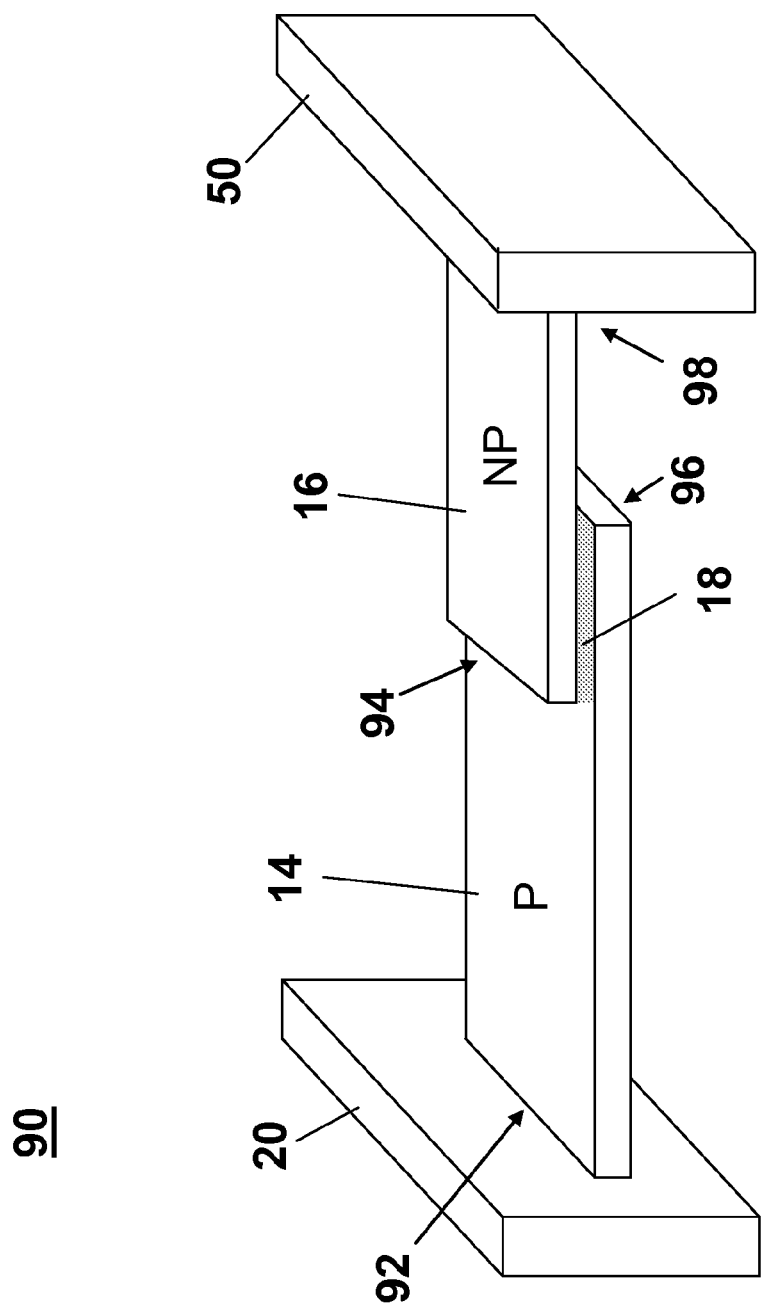
FIG. 13 is an illustration of an example configuration of a self-exciting, self-sensing piezoelectric cantilever sensor having an anchored non-piezoelectric portion and a non-anchored piezoelectric portion.

FIG. 13 is an illustration of an example configuration 90 of an anchored piezoelectric cantilever sensor comprising two base portions 20, 50, wherein the piezoelectric portion 14 is attached to the base portion 20 and the non-piezoelectric portion 16 is attached to the base portion 50. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The distal end 98 of the non-piezoelectric portion 16 extends beyond the distal end 96 of the piezoelectric portion 14. The proximate end 92 of the piezoelectric portion 14 extends beyond the proximate end 94 of the non-piezoelectric portion 16.

Figure 14:
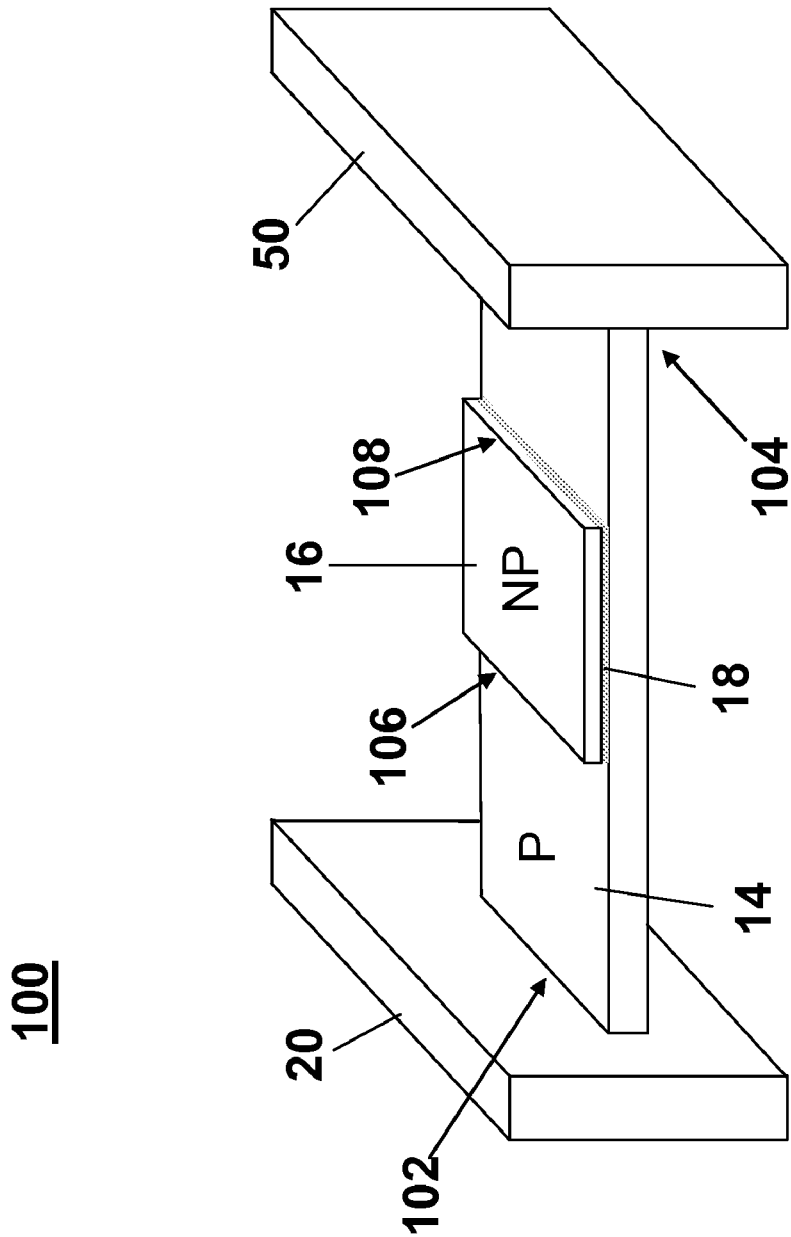
FIG. 14 is an illustration of an example configuration of a self-exciting, self-sensing piezoelectric cantilever sensor, wherein the non-piezoelectric layer is not attached to either base portion.

FIG. 14 is an illustration of an example configuration 100 of an anchored piezoelectric cantilever sensor comprising two base portions 20, 50, wherein the non-piezoelectric portion 16 is not attached to either base portion 20 or base portion 50. In the configuration depicted in the piezoelectric cantilever sensor 100, the proximate end 102 of the piezoelectric portion 14 is attached to the base portion 20 and the distal end 104 of the piezoelectric portion 14 is attached to the base portion 50. The proximate end 102 of the piezoelectric portion 14 extends beyond the proximate end 106 of the non-piezoelectric portion 16 and the distal end 104 of the piezoelectric portion 14 extends beyond the distal end 108 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 15:
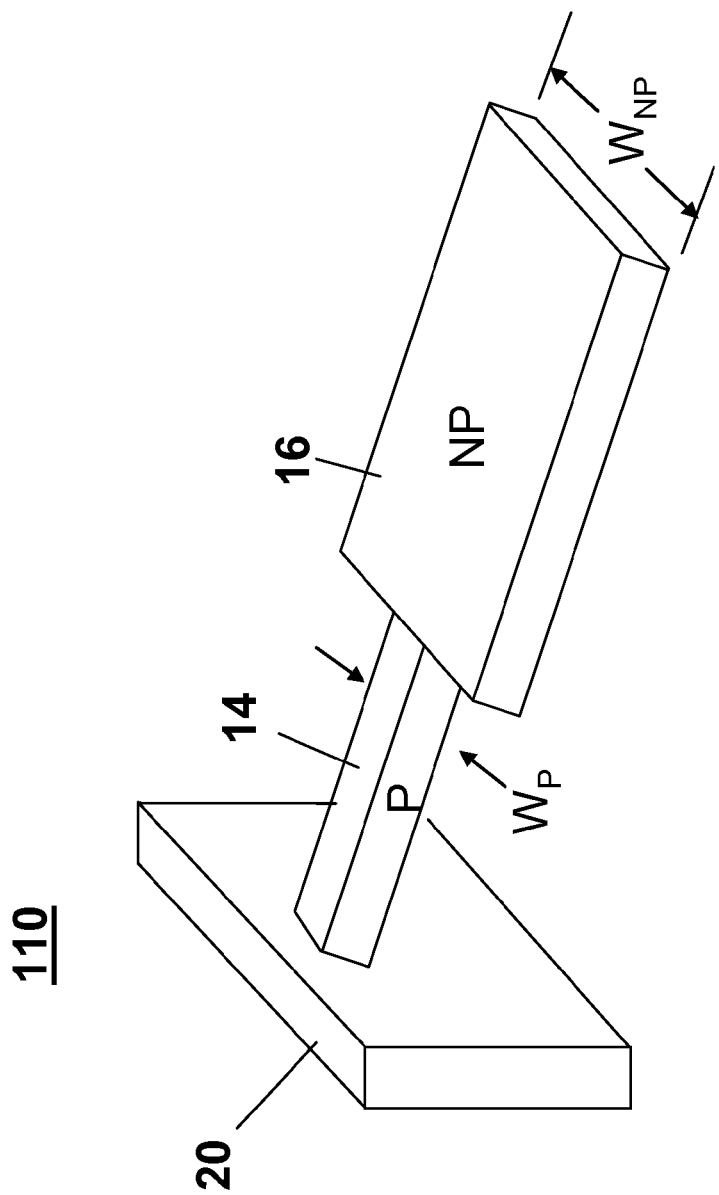
FIG. 15 is illustration of another example configuration of a self-exciting, self-sensing piezoelectric cantilever sensor wherein the piezoelectric portion has a different width than the piezoelectric portion.

FIG. 15 is an illustration of an example configuration 110 of an unanchored piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16. The configuration 110 depicted in FIG. 15 is similar to the configuration 12 depicted in FIG. 1, with the exception that $W_P$ is less than $W_{NP}$. According, the piezoelectric cantilever sensor 110 depicts an embodiment of an unanchored, overhang, piezoelectric cantilever sensor. The piezoelectric portion 14 is coupled to the non-piezoelectric portion 16 via adhesive portion (adhesive portion not shown in FIG. 15). The adhesive portion is positioned between the overlapping portions of the piezoelectric portion 14 and the non-piezoelectric portion 16. The piezoelectric portion 14 is coupled to a base portion 20.

Figure 16:
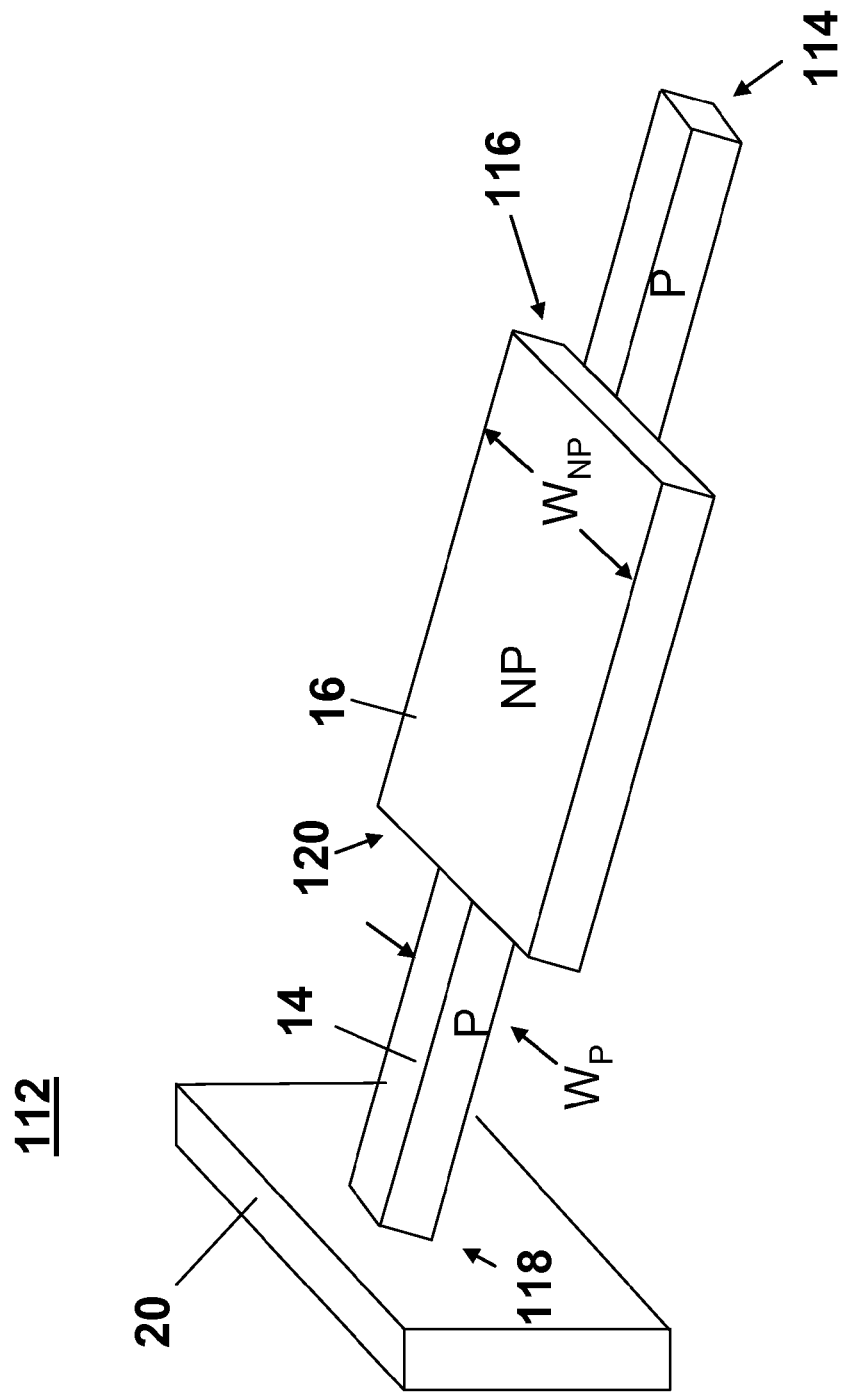
FIG. 16 is an illustration of an example configuration of a self-exciting, self-sensing piezoelectric cantilever sensor comprising a piezoelectric layer and a non-piezoelectric layer, wherein the width, of the piezoelectric layer is less than the width of the non-piezoelectric layer 16, and the distal end of the piezoelectric layer extends beyond the distal end of the non-piezoelectric layer and the proximate end of the piezoelectric layer extends beyond the proximate end of the non-piezoelectric layer.

FIG. 16 is an illustration of an example configuration 112 of an unanchored piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16, and wherein the distal end 114 of the piezoelectric portion 14 extends beyond the distal end 116 of the non-piezoelectric portion 16 and the proximate end 118 of the piezoelectric portion 14 extends beyond the proximate end 120 of the non-piezoelectric portion 16. The configuration 112 depicted in FIG. 16 is similar to the configuration 42 depicted in FIG. 6, with the exception that $W_P$ is less than $W_{NP}$. The piezoelectric portion 14 is coupled to the non-piezoelectric portion 16 via adhesive portion (adhesive portion not shown in FIG. 16). The adhesive portion is positioned between the overlapping portions of the piezoelectric portion 14 and the non-piezoelectric portion 16. The piezoelectric portion 14 is coupled to the base portion 20.

Figure 17:
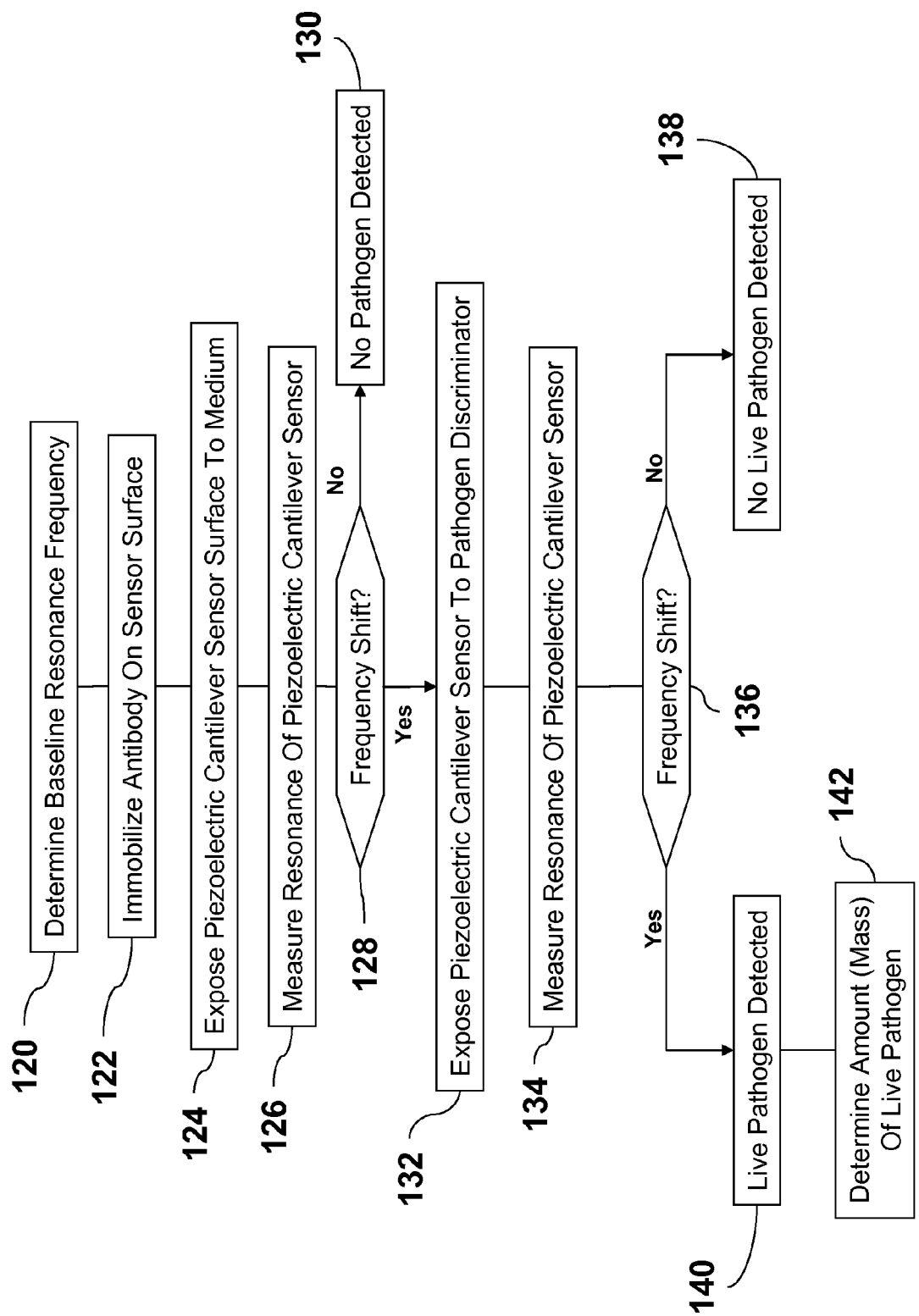
FIG. 17 is a flow diagram of an example process for detecting pathogens via a mass detecting device.

FIG. 17 is a flow diagram of an example process for detecting a live pathogen utilizing the piezoelectric cantilever sensor. The piezoelectric cantilever sensor can be configured in accordance with the descriptions provided above, or configured in accordance with any appropriate variant thereof. The baseline resonance frequency of the piezoelectric cantilever sensor is determined at step 120. The baseline resonance frequency is the resonance frequency of the piezoelectric cantilever sensor having no analyte (e.g., pathogen) accumulated thereon. When the piezoelectric material of the piezoelectric portion of the piezoelectric cantilever sensor is excited, the non-piezoelectric portion of the piezoelectric cantilever sensor flexes to accommodate the strain caused in the piezoelectric material. When the frequency of excitation is the same as the natural frequency of the underlying mechanical structure, resonance occurs. This resonance frequency determines the baseline resonance frequency.

The piezoelectric cantilever sensor is prepared to receive a pathogen at step 122. In an example embodiment, an analyte attractor is applied to the non-piezoelectric portion of the piezoelectric cantilever sensor. In an example embodiment, at step 122, an antibody known to bind to a specific pathogen (pathogen-specific antibody) is applied to (immobilized on) the non-piezoelectric portion of the piezoelectric cantilever sensor. The antibody is specific to a pathogen. Thus the antibody will selectively attach to a target pathogen and not attach to other substances. For example, the non-piezoelectric portion of the piezoelectric cantilever sensor can comprise an antibody for detecting food-borne pathogens, pathogens in food and water, cell types in body fluids (e.g., circulating tumor cells), or a combination thereof. In various example embodiments, the piezoelectric cantilever sensor is immobilized with the antibody against pathogenic bacteria ATCC 43251, to detect *Listeri monocytogenes*, the antibody against pathogenic bacteria ATCC 700375 to detect *E. coli* O157:H7, and/or the antibody against pathogenic bacteria ATCC 31194, to detect *Salmonella enteritidis*.

Immobilization of antibodies on the sensor surface can be accomplished in various ways. For example, antibodies can be immobilized on the sensor surface via chemical bonding using zero length cross linkers, or Protein G, on an Au (gold)-coated sensor. In an example embodiment, piezoelectric cantilever sensors having antibodies immobilized thereon are preserved and stored for subsequent use. In an example scenario, once the sensor surface is immobilized with an antibody, it will be dipped in a stabilizer solution (e.g., Stabil-Guard available from Sur-Modics, for example) and air dried in a vacuum desiccator, or the like, at approximately 20° C. for approximately 4 hours. The piezoelectric cantilever sensor is then sealed in a moisture proof container and stored at room temperature. It has been observed that this preservation and storage technique maintains the robustness of the piezoelectric cantilever sensor for several weeks. Longer storage times (e.g., predicatively up to 12 months) can be obtained by refrigerating the prepared sensor.

After antibodies, which can include a single antibody type or multiple types of antibodies directed to respective types of pathogens, have been immobilized on the piezoelectric cantilever sensor surface, the piezoelectric cantilever sensor surface is exposed to a medium at step 124. The medium can comprise any appropriate medium, such as a liquid, a gas, a combination of a liquid and a gas, or a vacuum, for example. The medium can comprise food samples, such as for example, spinach, lettuce, bean sprouts, ground beef, eggs, fruits, etc. The food samples can be suspended or dissolved in a liquid, mixed in a gas, or the like. The sensor is exposed to a medium that potentially contains the target pathogen. However, the medium can contain the target pathogen, can contain no target pathogen, or can contain a combination of target pathogen and non-target pathogen (pathogens other than the target pathogen). The medium does not require cleaning to remove debris.

During exposure, target pathogens (if present in the medium) will attach to the sensor antibodies immobilized on the sensor surface. During exposure, the medium can exhibit a wide variety of flow conditions which can be exploited to achieve selectivity. Additionally or alternatively, the sensor surface can be vibrated (via electromechanical stimulation) to achieve selectivity. If a target pathogen is present in the medium, the target pathogen will bind to the antibodies immobilized on the non-piezoelectric portion of the piezoelectric cantilever sensor. The bond will be relatively strong. If non-target analytes, such as non-target pathogens or debris, attach to the sensor surface, the vibration due to medium flow, and/or vibration resulting from exciting the sensor, will tend to knock loose the non-target analytes. However, because the bond between the antibody and the target pathogen is relatively stronger, the target pathogens remain bonded to the antibodies immobilized on the surface of the sensor. Thus, non-specific adsorption, that is adsorption of non-target pathogens, is reduced (and in some cases minimized or prevented entirely) due to flow and active sensor surface vibration. In an example embodiment, measurements are made under continuous vibration of the sensor surface at approximately 900 kHz and several nanometers in amplitude. And, although the presence of non-target entities influences the kinetics of attachment, the overall steady state response is unaffected.

When target pathogens are contained in the medium, both dead and live target pathogen cells bind to the immobilized antibody on the sensor surface. As described above, accumulation (e.g., binding) of the target pathogen on the non-piezoelectric portion of the piezoelectric cantilever sensor will result in a change in stiffness of the piezoelectric cantilever sensor and/or an increase the mass of the piezoelectric cantilever sensor, which will decrease the resonance frequency of the piezoelectric cantilever sensor. The resonance frequency of the piezoelectric cantilever sensor is measure at step 126. The resonance frequency can be measured by any appropriate means, such as an operational amplifier, an impedance analyzer, a spectrum analyzer, an oscilloscope, a network analyzer, an oscillator circuit, or the like, for example.

At step 128, the resonance frequency measured at step 126 is compared with the baseline resonance frequency (step 120). If no shift in resonance frequency is observed (at step 128), it is determined, at step 130, that no pathogens have accumulated on the sensor. Thus, no pathogens are detected. If, at step 128, a frequency shift is observed, it is determined that pathogens have accumulated on the sensor. Thus, pathogens are detected. At this point, live and dead pathogen cells may have accumulated on the sensor surface. To determine if live pathogen cells have accumulated on the sensor surface, the sensor surface is exposed to a pathogen discriminator, providing the ability to discriminate between live pathogen cells and dead pathogen cells.

At step 132, the surface of the piezoelectric cantilever sensor is exposed to a pathogen discriminator. Optionally, prior to exposing the sensor surface to a pathogen discriminator, the sensor surface can be rinsed. The pathogen discriminator provides the ability to discriminate between live and dead cells. In an example embodiment, the pathogen discrimination comprises a fluorescent molecule, or dye, such as, for example, intracellular pH indicating molecule (2',7'-bis-(2-carboxyethyl)-5-(and -6)-carboxyfluorescein, acetoxymethyl ester, BCECF-AM that partitions and accumulates in live cells, and not in dead cells. The resulting change in mass due to BCECF-AM accumulation, due to its high charge per molecule upon internalization, will cause a change in sensor resonance frequency thus providing a measure for the presence of live pathogens. Although BCECF-AM diffuses into dead cells, it does not accumulate because esterase activity and metabolic energy are required to hydrolyze uncharged BCECF-AM to charged and fluorescent BCECF.

The dye, BCECF-AM, is utilized as an intracellular pH dye. In an example embodiment, BCECF-AM, is loaded into a cell at a concentration of 1 to 10 µM. In another example embodiment, the pathogen discriminator, BCECF-AM, is loaded into a call at a concentration as high as 1 mM. In both live and dead cells, the transport of BCECF-AM is by trans-membrane passive diffusion. In live cells, intracellular esterases hydrolyze BCECF-AM into BCECF which has 4 to 5 charges at pH 7, thus entrapping it within the cell. Since the diffusing species loses identity, further transport occurs resulting in an accumulation of the dye within live cells. A maximum concentration is reached at equilibrium with intracellular charges and possibly membrane potential. In the case of dead cells, esterases are absent or of very low activity, and the cleaving does not take place allowing intracellular concentration to reach the same concentration as extracellular value. Thus there will be an increase in mass of cells on the sensor in proportion to the live cell concentration and concentration of BCECF-AM used. It is estimated that cell mass will increase by ~1%. If there is one cell attached to the sensor, the added mass would be 10 fg, which is within the measurable range of piezoelectric cantilever sensor. It is further estimated that 1 pg ($10^{-12}$ g) of live pathogen will accumulate as much as 10 femtograms of BCECF. In accordance with this estimation, a single live cell is detectable. The high sensitivity of the piezoelectric sensor implies that a single pathogen is measurable in a sample as small as a few milliliters (mL).

Subsequent to exposure to the pathogen discriminator, the resonance frequency of the piezoelectric cantilever sensor is measured at step 134. If live pathogen cells have attached to the sensor surface, and the pathogen discriminator has diffused and accumulated into the live cells, the mass accumulated on the sensor surface will have increased. Accordingly, the resonance frequency measurement at step 134 will indicate this increase in mass.

At step 136, the resonance frequency measured at step 126 is compared with the resonance frequency measured at step 134. If no shift in resonance frequency is observed (at step 136), it is determined, at step 138, that no live pathogens have accumulated on the sensor. If, at step 136, a frequency shift is observed, it is determined, at step 140, that live pathogens have accumulated on the sensor. At step 142, the amount of mass of live pathogen that has accumulated on the sensor surface is determined in accordance with the frequency shift measured at step 134, the type of pathogen detected, the type of pathogen discriminator utilized, and the amount of pathogen discriminator utilized.

Figure 18:
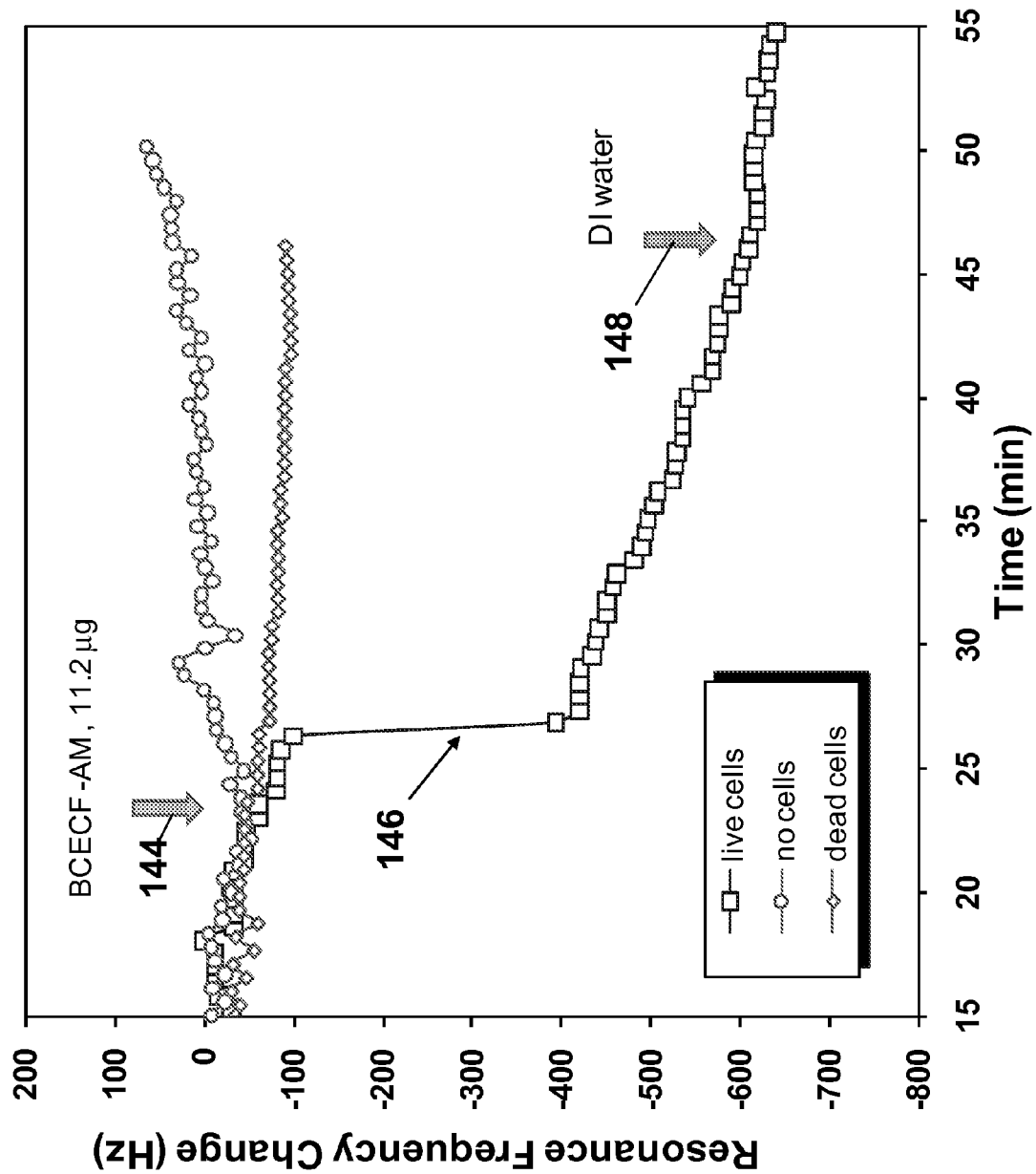
FIG. 18 is a plot indicating the results of an experiment showing that the pathogen discriminator partitions preferentially into live pathogens cells and does not partition preferentially into dead pathogen cells.

Various experiments have been conducted utilizing various configurations of the piezoelectric cantilever sensor to detect live pathogens. FIG. 18 is a plot indicating the results of an experiment showing that the intracellular pH dye, BCECF-AM, partitions preferentially into live cells and does not partition preferentially into dead cells. The piezoelectric cantilever sensor utilized was of an overhang design (3 mm PZT, 0.7 mm notch and 1 mm overhang) coated with 1% polylysine solution on a 1 mm$^2$ overhang section. After air drying, the sensor surface was dipped in a 300 µL solution containing approximately $10^8$ E. coli (strain JM101) cells. The cells were allowed to attach to the positively charged polylysine surface. The sensor was then installed in a flow cell and deionized (DI) water was allowed to recirculate at a rate of 0.15 mL/min. After the sensor resonance frequency stabilized (near 794 kHz), 11.2 µg of BCECF-AM was introduced into the flow loop at t=23 minutes, as depicted by the arrow 144 in FIG. 18. After approximately 5 minutes a rapid decrease in resonance frequency is observed on the graph (depicted as arrow 146). The decrease in resonance frequency is due to accumulation of the dye into the live E. coli cells. After approximately 22 minutes thereafter, a change of approximately 550 Hz was observed, and the flow medium was changed to deionized (DI) water (arrow 148), and the resonance frequency decrease rate became smaller and ultimately the resonance frequency stabilized. Two control experiments are also included. The same sensor was immobilized with killed E. coli (strain JM101) cells at the same concentration, and was exposed to 11.2 µg of BCECF-AM. As seen in FIG. 18, a small drift of approximately 60 Hz was observed. No rapid change in resonance frequency was observed. A sensor coated with polylysine and without any immobilized cells showed no significant resonance frequency shift.

Figure 19:
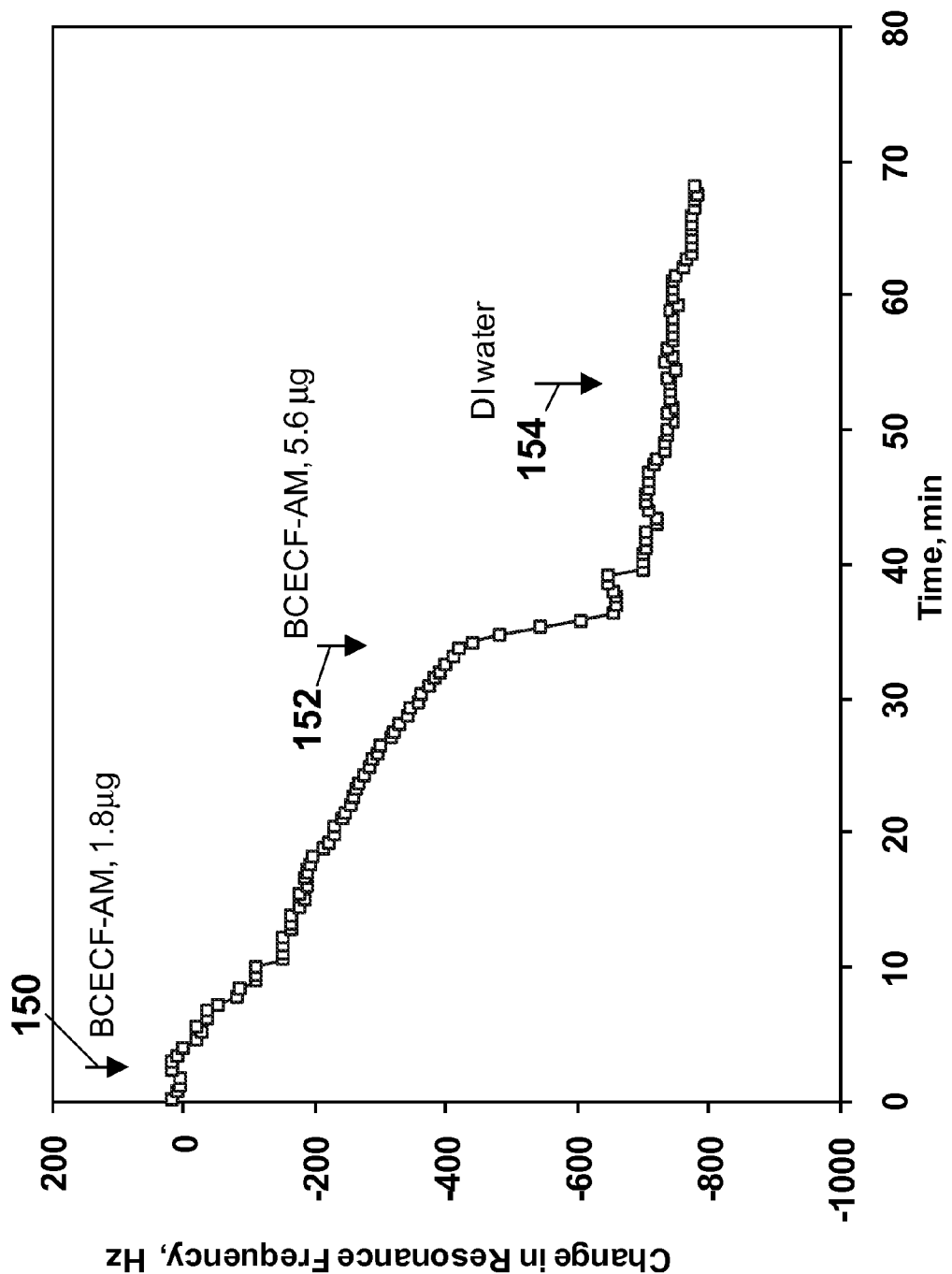
FIG. 19 is a plot indicating the results of an experiment showing that the mass detection device response is proportional to the concentration of pathogen discriminator used.

FIG. 19 is a plot indicating the results of an experiment showing that the piezoelectric cantilever sensor response is proportional to the concentration of pathogen discriminator used. Again, the intracellular pH dye, BCECF-AM, was used as the pathogen discriminator. As evidenced in FIG. 19, the transport of BCECF-AM into live cells directly depends on the concentration of BCECF-AM. The transport flux across the cell plasma membrane is proportional to concentration difference that is present between the extracellular and intracellular environments. After loading the sensor with live cells (E. coli, strain JM101), the sensor was stabilized in a flow cell with deionized (DI) water flowing at 0.15 mL/min. At t=3 min, 1.8 µg of BCECF-AM, prepared per vendor protocol, was injected into the flow loop (indicated by arrow 150). As shown in FIG. 19, the resonance frequency of the sensor decreased rapidly followed by a more gradual decrease. At t=32 min, a further addition of 5.6 µg of BCECF-AM was added to the flow loop (indicated by arrow 152). Again, the resonance frequency decreased rapidly followed by a slower decrease. The response reached steady state at approximately t=50 min. An overall shift down of resonance frequency of approximately 740 Hz was obtained. Introduction of DI (deionized) water in flush mode (indicated by arrow 154) resulted in a very small further decrease (approximately 25 Hz) in resonance frequency and the sensor response stabilized. Additional control experiments (not shown) utilizing a piezoelectric cantilever sensor immobilized with killed E. coli and a piezoelectric cantilever sensor coated with only polylysine, exhibited no significant resonance frequency change (less than 50 Hz) for the same set of BCECF-AM concentrations.

The experiment depicted in FIG. 18, used 11.2 µg BCECF-AM, which caused a very rapid, almost step-like, response in change in resonance frequency. The decreased response rate shown in FIG. 19, is due to the lesser concentration of BCECF-AM used (1.8 µg), and confirms that pathogen discriminator concentration can be selectively tailored for a desired sensitivity.

In an example embodiment, rather than exposing pathogens to a pathogen discriminator, pathogen cells are allowed to grow on the sensor surface and a detected change in mass is indicative of the presence of live cells. The extreme sensitivity to changes in mass obtainable with the piezoelectric cantilever sensor allows rapid detection of growth. For example, a single doubling of an attached pathogen will cause a large resonance frequency change because a single cell is approximately 1 pg and the piezoelectric cantilever sensor can measure fg changes of mass. Growth, in nutrient rich medium, should result in an exponential mass increase on the sensor. For example, the exponential increase in mass can be modeled by the equation, $m=m_0 \exp(\mu_m t)$, where m is the instantaneous mass of actively growing cells on the sensor, $m_0$ is the initial mass that attached to the sensor, $\mu_m$ is a specific growth rate, and t is time since growth started after an initial lag phase. Because resonance frequency change ($\Delta f$) is proportional to mass attached (for small masses), the resonance frequency change should follow a relationship such as: $\Delta f = \Delta f_0 \exp(\mu_m t)$ where $\Delta f$ is the instantaneous resonance frequency change since growth started. Accordingly, observed changes in mass are dependent on specific growth rate ($\mu_m$) and the initial number of pathogens.

It is to be understood that even though numerous characteristics and advantages of detecting and measuring live pathogens utilizing a piezoelectric cantilever sensor have been set forth in the foregoing description, together with details of the structure and function of the piezoelectric cantilever sensor, the disclosure is illustrative only, and changes may be made in detail, especially in matters of shape, size and arrangement of parts of the piezoelectric cantilever sensor to the full extent indicated by the broad general meaning of the terms in which the appended claims are expressed. For example, the process of detecting live pathogen cells can accomplished with any appropriate detection device capable of detecting changes in mass, and thus, is not limited to the piezoelectric cantilever sensors described herein. However, the herein described piezoelectric cantilever sensor provides the ability to detect smaller changes in mass than other know devices. Thus, while detecting and measuring live pathogens utilizing a piezoelectric cantilever sensor has been described in connection with the various embodiments of the various figures, it is to be understood that other similar embodiments can be used or modifications and additions can be made to the described embodiment for performing the same function of detecting and measuring live pathogens utilizing a piezoelectric cantilever sensor without deviating therefrom. Therefore, detecting and measuring live pathogens utilizing a piezoelectric cantilever sensor should not be limited to any single embodiment, but rather should be construed in breadth and scope in accordance with the appended claims.

What is claimed:

1. A method for detecting a live pathogen, the method comprising:
exposing a mass detection device to a medium, the mass detection device configured to:

detect a change in mass accumulated thereon; and
prevent accumulation of non-target mass thereon via at least one of medium flow or vibration of a surface of the device;
measuring a first amount of mass accumulated on the mass detection device;
subsequently exposing the mass detection device to a pathogen discriminator, the pathogen discriminator capable of discriminating between live pathogen cells and dead pathogen cells;
measuring a second amount of mass accumulated on the mass detection device;
comparing the first amount with the second amount; and
when the second amount is greater than the first amount, determining that a live pathogen is detected.

2. The method in accordance with claim 1, wherein the first amount of mass is indicative of an amount of live pathogen cells and dead pathogen cells accumulated on the mass detection sensor.

3. The method in accordance with claim 1, wherein determining that a live pathogen is detected is an indication that the live pathogen has accumulated on the mass detection device.

4. The method in accordance with claim 1, wherein determining that a live pathogen is detected is an indication that the live pathogen was present in the medium.

5. The method in accordance with claim 1, wherein the pathogen discriminator causes an increase of mass of a live pathogen.

6. The method in accordance with claim 1, wherein the pathogen discriminator causes an increase in mass of a live pathogen via transmembrane passive diffusion.

7. The method in accordance with claim 1, wherein the pathogen discriminator comprises a pH indicating molecule.

8. The method in accordance with claim 1, wherein the pathogen discriminator comprises 2',7'-bis-(2-carboxyethyl)-5-(and-6)-carboxyfluorescein, acetoxymethyl ester.

9. The method in accordance with claim 1, further comprising:
prior to exposing the mass detection device to the medium, immobilizing on the mass detection device a pathogen-specific antibody known to bind to a specific pathogen.

10. The method in accordance with claim 9, wherein the live pathogen comprises the specific pathogen.

11. The method in accordance with claim 9, wherein the specific pathogen comprises at least one of *Escherichia coli*, *Listeri monocytogenes*, or *Salmonella enteritidis*.

12. The method in accordance with claim 9, wherein the pathogen-specific antibody comprises at least one of an antibody that binds to ATCC 43251, an antibody that binds to ATCC 700375, or an antibody that binds to ATCC 31194.

13. The method in accordance with claim 1, wherein the mass detection device comprises a piezoelectric cantilever sensor comprising:
a piezoelectric layer;
at least one base portion coupled to at least one of the piezoelectric layer and the non-piezoelectric layer;
a non-piezoelectric layer, wherein at least a portion of the piezoelectric layer is coupled to at least a portion of the non-piezoelectric layer such that the piezoelectric layer and the non-piezoelectric layer are not coextensive; and
electrodes operatively associated with the piezoelectric layer; and
at least a portion of the non-piezoelectric layer is exposed to the medium.

14. The method in accordance with claim 13, further comprising:
measuring the first amount of mass accumulated on the mass detection device by measuring, via the electrodes, a first resonance frequency of the sensor;
measuring the second amount of mass accumulated on the mass detection device by measuring, via the electrodes, a second resonance frequency of the sensor; and
comparing the first amount with the second amount by comparing the first resonance frequency with the second resonance frequency.

15. The method in accordance with claim 1, wherein an amount of live pathogen detected is equivalent to 1 pathogen per 1 mL of medium.

16. A method comprising:
exposing a mass detection device to a medium, the mass detection device configured to detect a change in mass accumulated thereon, and prevent accumulation of non-target mass thereon via at least one of medium flow or vibration of the surface of the device;
measuring a first amount of mass accumulated on the mass detection device;
subsequently exposing the mass detection device to 2',7'-bis-(2-carboxyethyl)-5-(and-6)-carboxyfluorescein, acetoxymethyl ester; measuring a second amount of mass accumulated on the mass detection device;
comparing the first amount with the second amount; and
when the second amount is greater than the first amount, determining that a live pathogen is detected.

* * * * *